United States Patent [19]

Wielinger et al.

[11] Patent Number: 5,190,862
[45] Date of Patent: Mar. 2, 1993

[54] CHROMOGENIC COMPOUNDS AND THE USE THEREOF AS ENZYME SUBSTRATES

[75] Inventors: Hans Wielinger, Weinheim; Gerd Zimmermann, Mannheim, both of Fed. Rep. of Germany

[73] Assignee: Boehringer Mannheim GmbH, Mannheim, Fed. Rep. of Germany

[21] Appl. No.: 776,590

[22] Filed: Oct. 11, 1991

Related U.S. Application Data

[62] Division of Ser. No. 175,838, Mar. 31, 1988, Pat. No. 5,108,890.

[30] Foreign Application Priority Data

Apr. 1, 1987 [DE] Fed. Rep. of Germany ....... 3710937

[51] Int. Cl.$^5$ .......................... C12Q 1/37; C12Q 1/44; C12Q 1/56
[52] U.S. Cl. ........................................ 435/23; 435/13; 435/19
[58] Field of Search ............... 435/13, 23, 19

[56] References Cited

U.S. PATENT DOCUMENTS 4,457,866  7/1984  Karges et al. ..................... 435/4
4,950,593  8/1990  Matta et al. ...................... 435/23

FOREIGN PATENT DOCUMENTS 0158254  10/1985  European Pat. Off. .

Primary Examiner—Robert A. Wax
Assistant Examiner—Stephen Walsh
Attorney, Agent, or Firm—Felfe & Lynch

[57] ABSTRACT

The present invention provides compounds of the general formula:

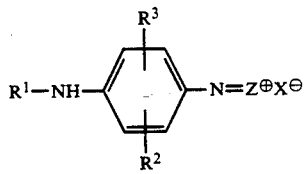

wherein $R^1$ is an amino acid residue or a residue of an oligopeptide in which the amino groups are optionally substituted by protective groups, $R^2$ and $R^3$, which are the same or different, are hydrogen atoms, a lower alkyl, lower alkoxy, carboxyl or lower alkoxycarbonyl radicals or carboxamido groups optionally substituted by lower alkyl or, if $R^2$ and $R^3$ are adjacent, can represent a —CH=CH—CH=CH— radical, Z is conjugated-through positively charged, bicyclic heterocyclic system and X is an anion of an organic or inorganic acid. The present invention also provides processes for the preparation of these compounds and diagnostic agents containing them for the determination of peptide bond-cleaving enzymes.

40 Claims, No Drawings

CHROMOGENIC COMPOUNDS AND THE USE THEREOF AS ENZYME SUBSTRATES

This is a divisional application of application Ser. No. 07/175,858, filed Mar. 31, 1988, now U.S. Pat. No. 5,108,890.

The present invention is concerned with chromogenic compounds which can be used as substrates for the detection and determination of peptide bond-cleaving enzymes with a process for their preparation and methods of using these.

Peptide bond-cleaving enzymes are those which are capable of hydrolyzing CONH bonds. These include transpeptidases, for example γ-glutamyl transpeptidase, peptidases, for example leucine arylamidase, and proteinases, for example cathepsins, chymotrypsin, collagenases, elastases, enterokinases, papain, trypsin, and, also, all proteases which participate in the course of blood coagulation and fibrinolysis. The enzymes which participate in the course of blood coagulation and fibrinolysis, as well as trypsin, chymotrypsin, leucine arylamidase and γ-glutamyl transpeptidase, have become very important in clinical chemistry for obtaining diagnostic evidence.

For the detection and the determination of these enzymes in body fluids, for example in blood, serum, plasma or urine, it is often important to obtain precise results as quickly as possible. Since the field of use for such detection and the determination processes is wide, it is necessary to have simple processes available. These processes must not be disturbed by the character of the sample. Such disturbances can be, for example, colorations in the case of icteroid samples, turbidities in the case of lipaemic samples and the like.

Previously known substrates for peptide bond-cleaving enzymes can be represented by the general formula:

$$R^1\text{—NH—R} \quad \text{(I)}$$

wherein $R^1$ is a residue of an amino acid or of an oligopeptide which possibly contains protected amino groups and R is the residue of a detectable compound which, with an amino group, has formed an amide bond with the carboxyl end of an amino acid or of an oligopeptide. In the case of the enzymatic cleavage of such substrates, there are obtained carboxylic acids $R^1$—OH (Ia) (amino acids or oligopeptides with free carboxyl function) and amines R—NH$_2$ (Ib).

As $R^1$, there are most frequently used individual amino acids to tetrapeptides. However, larger oligopeptides can also be used. In general, with a substrate of general formula I, there is offered to the enzyme the amino acid or amino acid sequence on which it also cleaves in the natural substrate and which, in the end, is mainly responsible for the specificity of the substrate for the enzyme. Representative of the numerous amino acids or amino acid sequences known from the scientific literature, the following are some especially interesting diagnostic examples: for transpeptidases, such as γ-glutamyl transpeptidase, the γ-glutamyl radical (Bergmeyer, "Methods of Enzymatic Analysis", 3rd edition, Volume III, 349–364, Verlag Chemie, 1983), for peptidases, such as leucine amonopeptidase, the leucine radical (Z. Klin. Chem. u. klin. Biochem. 10, 192/1972), for proteinases, such as trypsin, the N-terminal protected tetrapeptide Ile-Glu-Gly-Arg (Bergmeyer, "Methods of Enzymatic Analysis", 3rd edition, Volume V, 124–129, Verlag Chemie, 1984) and for proteases which participate in the processes of blood coagulation, such as thrombin, the N-terminal protected tripeptides Val-Pro-Arg and Gly-Pro-Arg and the like (Seminars in Thrombosis and Hemostasis, Volume 9, Number 3, 179–183/1983).

Amines R—NH$_2$ represent detectable compounds which are liberated by the action of peptide bond-cleaving enzymes on substrates of the general formula I. As a rule, these are compounds which, by bonding to an amino acid or an oligopeptide in a substrate of general formula I, undergo a displacement of the absorption maximum or of the fluorescence emission maximum to a shorter wavelength range, compared with the free compound R—NH$_2$. The compound R—NH$_2$ split off from the substrate thus absorbs light or emits fluorescence in a longer wave range.

In all, substrates of general formula I can be divided up, depending upon the nature of the detectable compounds liberated therefrom by enzymatic hydrolysis, into three categories.

The first category includes substrates which, after cleavage, give p-nitroaniline or a derivative hereof. Such substrates are, for example, the subject of U.S. Pat. Nos. 4,508,644; 4,665,016 and Federal Republic of Germany Patent Specification No. 33 11 287. The detectable compounds resulting by cleavage are yellow and are preferably measured at 405 nm to 420 nm.

However, such compounds have the disadvantage that they can be disturbed by numerous influences originating from the sample. Important disturbance factors are, for example, the inherent colors of sera, lipaemic turbidities, increased bilirubin values and the like. Therefore, substrates splitting off p-nitroaniline or p-nitroaniline derivatives are only of limited use. In dry chemical tests, which are measured by remission photometry, the above-mentioned influences disturb the substrates to such an extent that such substrates are of practically no use.

Substrates of the second category split off fluorescing compounds, such as, 7-amino-4-methylcoumarin, 4-trifluoromethyl-7-aminocoumarin, 4-methoxy-β-naphthylamine, β-naphthylamine, and 5-aminosophthalic acid dimethyl ester. Further fluorescing compounds which can be liberated from substrates for peptide bond-cleaving enzymes are mentioned in U.S. Pat. No. 4,457,866.

Because of the equipment needed for the fluorescence measurement, their use is problematical. Therefore, they have achieved no importance as substrates for routine measurements.

The third substrate category concerns those amides from which, by enzymatic action, there are split off aminophenols, phenylenediamines or other aromatic amines which, in the range of visible light, do not absorb sufficiently and, therefore, require a subsequent reaction for a color formation. For the color formation, there are mostly used oxidative coupling reactions, such detection principles being known, for example, from U.S. Pat. Nos. 4,588,836; 4,450,105; and 4,520,100.

The requirement of coupling the compounds split off from substrates of the third category with the use of subsequent oxidizing reaction makes their use complicated and limited. All substances contained in the sample which form a colored material by oxidation can disturb such detection reactions. These include, in particular, the bilirubin present in every plasma and serum sample. It must be excluded in the case of all tests which work according to the principle of oxidative coupling by means of a preceding reaction. Furthermore, oxidation agents can also have a disturbing effect by entering into the reactions preceding the actual substrate cleavage reaction. Thus, for example, the course of the coagulation cascades is influenced by oxidation agents.

Therefore, there is still a need for substrates for peptide bond-cleaving enzymes, especially for transpeptidases, peptidases and proteinases, which, when cleaved, form a colored material directly, the absorption maximum of which is clearly above 420 nm and the maximum absorption wavelength of which so differs from the maximum absorption wavelength of the substrate that there is obtained a signal which is satisfactory for the measurement of the enzyme activity.

It is an object of the present invention to provide such substrates.

Thus, according to the present invention, there are provided the new compounds of the general formula:-

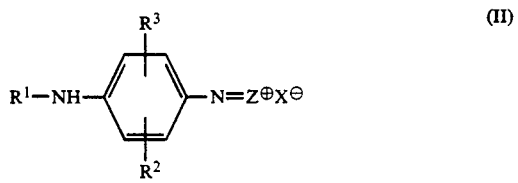

wherein $R^1$ is an amino acid residue or a residue of an oligopeptide in which amino groups are optionally substituted by protective groups, $R^2$ and $R^3$, which are the same or different, are hydrogen atoms, lower alkyl, lower alkoxy, carboxyl or lower alkoxycarbonyl radicals or carboxamido groups optionally substituted by lower alkyl or, if $R_2$ and $R_3$ are adjacent, can represent a —CH=CH—CH=CH— radical, Z a mesomerically and/or tautomerically stabilized positively-charged, bicyclic heterocyclic system and X is an anion of an organic or inorganic acid.

The amino acid or oligopeptide residue of the substrates according to the present invention can be selected according to the enzyme to be determined. The amino acids can hereby be $\alpha$-, $\beta$- or $\gamma$-amino acids containing 2 to 15 and preferably 2 to 10 carbon atoms. If the amino acids are chiral compounds, then they can be present in the D- or L-form or also as a racemate. Amino acids of natural origin, such as they occur in proteins and peptide antibiotics, are preferred. However, there can also be used synthetic amino acids, for example pipecolic acid, cyclohexylalanine, phenylglycine, $\alpha$-aminocyclohexylcarboxylic acid, hexahydrotyrosine, norleucine or ethionine. As examples of enzymes which react with the substrates of general formula II, in which $R^1$ is an amino acid residue, there may be mentioned $\gamma$-glutamyltranspeptidase, which reacts with a glutamyl residue; trypsin, which cleaves substrates with an arginine residue; aminopeptidase M, which hydrolyses substrates with an aliphatic amino acid residue, for example alanine; and chymotrypsin which recognises substrates containing phenylalanine.

Oligopeptide residues in the meaning of $R^1$ contain 2 to 10, preferably 2 to 6 and especially preferably 2 to 4 amino acid units. The amino acids of the oligopeptide can be of natural and/or synthetic origin and correspond to the above-given definition for appropriate amino acids in compounds of general formula II.

Depending upon the enzyme to be determined, from the literature (e.g. Seminars in Thrombosis and Hemostasis, Vol. 9, No. 3, pp. 179-183/1983; IUPAC Enzyme Nomenclature, 1984, Academic Press, Orlando; and T. E. Barman, "Enzyme Handbook", 1969, Supplement I, 1974, Springer-Verlag, Heidelberg) are known appropriate amino acid and oligopeptide residues which can be used as radicals $R^1$ in substrates of general formula I. They can find use analogously to the substrates of general formula II according to the present invention.

In the substrates of general formula II, the terminal and/or other possibly present amino groups of the amino acid or oligopeptide residue $R^1$ can be present in free form. However, they can possibly also be substituted by protective groups.

Examples of amino protective groups include acyl, oxycarbonyl, thiocarbonyl, sulphonyl, sulphenyl, vinyl, cyclohexenyl, phosphoryl and carbamoyl groups, acyl, sulphonyl and oxycarbonyl groups being preferred.

The acyl radicals can be those derived from aliphatic and aromatic carboxylic acids, for example formyl, acetyl, propionyl, isobutyryl, benzoyl and naphthoyl radicals, formyl, acetyl and benzoyl radicals being especially preferred.

Preferred oxycarbonyl radicals include the benzyloxycarbonyl, tert.-butoxycarbonyl, ethoxycarbonyl and p-methoxybenzyloxycarbonyl radicals.

Sulphonyl groups include, for example, residues of aliphatic sulphonic acids containing up to 6 carbon atoms, preferably the methanesulphonyl and ethanesulphonyl radicals, and, for example, radicals derived from aromatic sulphonic acids, preferably the benzenesulphonyl, toluenesulphonyl and naphthylsulphonyl radicals.

In the definition of the substituents $R^2$ and $R^3$ of the p-phenylenediamine moiety of the compounds of general formula II, a lower alkyl radical is a straight or branched alkyl radical containing up to 6 and preferably up to 4 carbon atoms, especially preferred radicals including methyl, ethyl, isopropyl and isobutyl.

A lower alkoxy radical in the definition of $R^2$ and $R^3$ means a straight or branched alkoxy radical containing up to 6 and preferably up to 4 carbon atoms, preferred lower alkoxy radicals including methoxy, ethoxy, propoxy, isobutoxy and tert.-butoxy.

The preceding definition for the lower alkoxy radical also applies to the lower alkoxy moiety in the lower alkoxycarbonyl radicals of $R^2$ and $R^3$.

In the same way, the above-given definition of the lower alkyl radicals also applies to the lower alkyl substituents of a carboxamido group $R^2$ and $R^3$.

The acid anion $X^-$ is an anion of any organic acid or mineral acid, anions of stronger organic or inorganic acids being preferred. Especially preferred anions include acetate, trifluoroacetate, oxalate, methanesulphonate, sulphate, chloride, bromide and perchlorate ions.

The through-conjugated, positively charged, bicyclic, heterocyclic system in the definition of Z can be any one of a plurality of radicals, those heterocyclics which contain nitrogen or nitrogen and sulphur as heteroatoms being preferred. In particular, those systems Z are preferred for compounds of general formula II according to the present invention which are represented by the general formula:

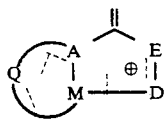

in which A, M, D and E are carbon or nitrogen atoms, whereby, insofar as they are not bridgehead atoms, carbon atoms can optionally be substituted by oxygen, lower alkyl, lower alkoxy, aryl, aralkyl or aryloxy and nitrogen optionally by lower alkyl, aralkyl or aryl and Q is an unsaturated hydrocarbon chain containing 3 to 5 members which is optionally interrupted by nitrogen or sulphur atoms or contains such heteroatoms at the beginning of end of the chain, carbon atoms optionally being substituted by lower alkyl, lower alkoxy, aralkyl, aryloxy or aryl and/or nitrogen atoms optionally by lower alkyl, aralkyl or aryl, two neighbouring lower alkyl radicals optionally forming a saturated alkylene radical containing 3 to 5 carbon atoms, the sum of the heteroatoms in the bicyclic radical being at most 3. Especially preferred are such systems Z of the general formula III in which one or two of A, M, D and E are nitrogen, the other being carbon atoms wherein D and E can optionally be substituted as indicated above.

The broken line in general formula III means that the positive surplus charge is not localized only on a particular atom of the bicyclic system but rather is present distributed by mesomerism or tautomerism over the cyclic conjugated part of the molecule.

As bridgehead atoms are designated the atoms A and B which simultaneously belong to both rings of the bicyclic system. In the radical Z of the substrates according to the present invention, they are not substituted by other atoms or radicals.

The atoms D and E are not bridgehead atoms. When either of these is carbon, it may be substituted by an oxygen atom, forming, e.g. a carbonyl group.

Lower alkyl or lower alkoxy radicals which can substitute non-bridgehead-forming carbon or nitrogen atoms in the definition of D and E are those which contain up to 6 and preferably up to 4 carbon atoms, especially preferred radicals being methyl, ethyl, n-propyl, methoxy, ethoxy and n-propoxy.

Aryl or aryloxy radicals which can be present as substituents on carbon or nitrogen atoms in the definition of D and E are preferably phenyl, naphthyl, phenoxy or naphthoxy. These can, in turn, optionally be substituted by one or more alkyl or alkoxy radicals containing up to 6 and preferably up to 4 carbon atoms and/or by one or more halogen atoms, such as fluorine, chlorine, bromine or iodine and preferably chlorine or bromine. As aryl and aryloxy substituents, phenyl and phenoxy are especially preferred.

Aralkyl radicals as optional substituents of carbon and nitrogen atoms in the definition of D and E are especially phenylmethyl and naphthylmethyl radicals, the phenylmethyl group being especially preferred.

By a 3 to 5-membered unsaturated hydrocarbon chain in the definition of Q, which is optionally interrupted by nitrogen or sulphur atoms or contains such heteroatoms at the beginning or end of the chain, there is preferably to be understood a chain which, by anellation to the other ring system, forms a five- or six-membered ring. This anellated ring system contains one or more double bonds which are conjugated to the double bond system of the other ring so that the positive surplus charging of the heterocyclic system Z can be exchanged by mesomerism or tautomerism between the two rings. Especially preferred ring systems for the Q-containing ring of the bicycle Z are the thiazolium and pyridinium systems.

As lower alkyl, lower alkoxy, aryloxy, aralkyl and aryl radicals, which can be present as substituents on the carbon or nitrogen atoms of the unsaturated chain Q, there can be used the same radicals as described above for carbon and nitrogen atoms in the definition of D and E.

When, within Q, two neighbouring lower alkyl radicals are present as substituents of carbon and/or nitrogen atoms, it is possible for these to represent a saturated alkylene radical containing 3 to 5 carbon atoms and thus to form a ring condensed on to Q. Alkylene radicals with 3 or 4 carbon atoms are preferred which form a five- or six-membered ring. Especially preferred is a so condensed cyclopentane or cyclohexane ring.

Especially preferred are those compounds of general formula II in which Z is one of the following radicals:

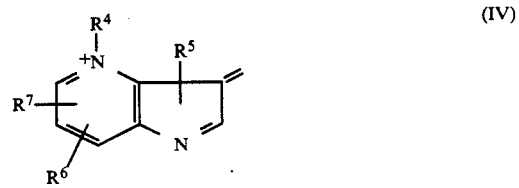
(IV)

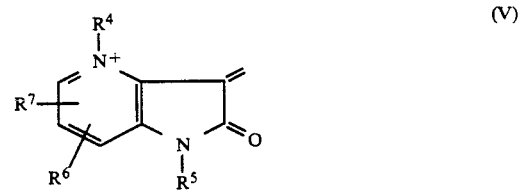
(V)

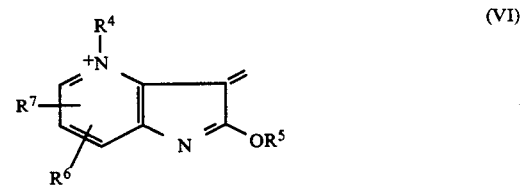
(VI)

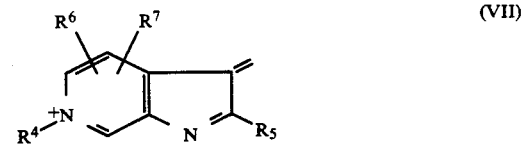
(VII)

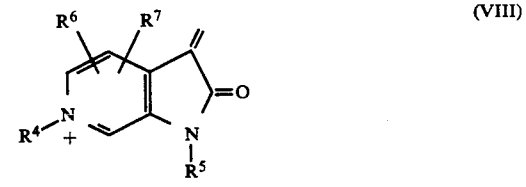
(VIII)

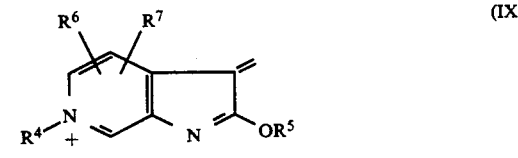
(IX)

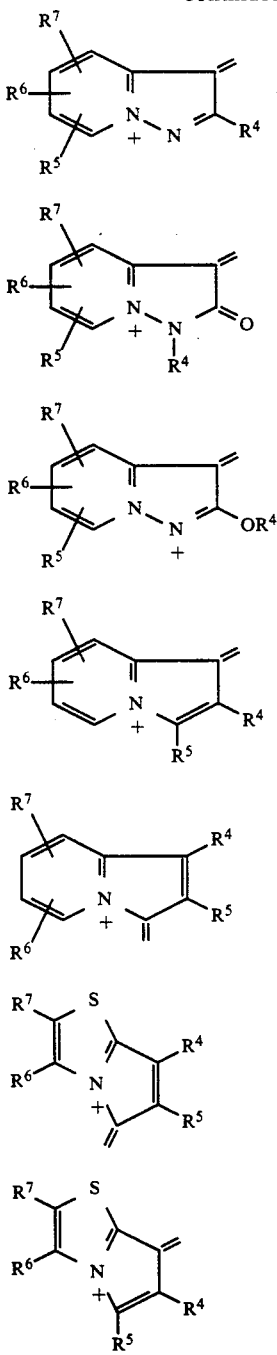

(X)

(XI)

(XII)

(XIII)

(XIV)

(XV)

(XVI)

wherein $R^4$, $R^5$, $R^6$ and $R^7$, which can be the same or different, are hydrogen atoms or lower alkyl, lower alkoxy, aralkyl, aryloxy or aryl radicals.

As lower alkyl, lower alkoxy, aralkyl, aryloxy and aryl radicals in the definition of $R^4$-$R^7$, one uses the same radicals as mentioned above for the substituents in the definition of D, E and Q of general formula III.

Especially preferred compounds of general formula II are those which, as through-conjugated, positively-charged bicyclic heterocyclic systems Z, contain one of the radicals of general formulae V, VIII, XI, XII, XIV or XV.

The compounds of the general formula II are new.

From the literature are known condensations of aromatic or heteroaromatic nitroso compounds with phenols, anilines, methylene bases and their precursors, corresponding methyl-substituted, quaternary nitrogen heterocycles, for example 2- or 4-picoline iodomethylate, 2-methyl-1-arylquinolinium salts, pyrazolones or imidazolo-(1,2a)-pyridin-2-one (Houben-Weyl, Volume 10/1, page 1079 et seq.; Chem. Ber., 90, 2792/1957; J. Chem. Soc., 914/1951; F. Hamer in "Cyanine and related dyes", The Chemistry of Heterocyclic Compounds, A. Weissberger ed., Volume 18, page 443 et seq.; H. Stamm in "Methodicum Chimicum", F. Zymalkowsky ed., Volume 6, Georg Thieme Verlag, Stuttgart, 1975, page 33; Bull. Soc. Chim. Belg., 58, 498/1949; J. Amer. Chem. Soc., 66, 1805/1944). These condensations take place with heating and basic catalysis by, for example, piperidine, sodium hydroxide or sodium carbonate. In individual cases, for example when using quaternary ammonium salts, the reaction can also take place without catalysis.

From Houben-Weyl, Volume 10/1, page 1081 et seq. are also known condensations of 3,5-diphenyl-2-nitrosopyrrole with 2,4-diphenylpyrrole and of nitrosobenzene with 2,4-diketopiperazine, which take place in the presence of acetic anhydride with heating. However, such drastic reaction conditions cannot be used in the case of compounds which, as in the present application, contain amino acid components as structural elements.

Therefore, it is surprising that it is possible to obtain compounds of general formula II by the reaction of nitroso compounds of the general formula:

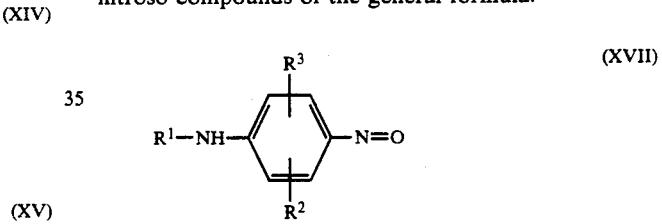

(XVII)

wherein $R^1$ is an amino acid residue or a residue of an oligopeptide in which amino groups are substituted by protective groups and $R^2$ and $R^3$, which are the same or different, are hydrogen atoms or lower alkyl, lower alkoxy, carboxyl or lower alkoxycarbonyl radicals or carboxamido groups optionally substituted by a lower alkyl radical or, when $R^2$ and $R^3$ are adjacent, a —CH=CH—CH=CH— radical, under mild conditions and acidic catalysis with compounds of the general formula:

Z'—H                                          (XVIII)

wherein Z' is an uncharged, bicyclic, heterocyclic system, and optionally with the subsequent complete or partial removal of amino protective groups.

The reaction between compounds of general formulae XVII and XVIII takes place at a temperature of from $-20°$ to $+50°$ C. and preferably of from $+10°$ to $+25°$ C.

As acidic catalysts, there can be used organic acids or mineral acids. Aprotic and protic solvents can be used. Preferred aprotic solvents include, for example, dimethylformamide and methylene chloride and preferred protic solvents include alcohols, for example methanol or ethanol. However, acetic acid is especially preferred as a reaction medium, in which case this acid serves not only as a solvent but also as a catalyst.

Reactions of aromatic nitroso compounds with heterocyclic, bicyclised compounds of general formula XVIII under the above-mentioned conditions were hitherto not known. This includes reactions of compounds of general formula XVII with those bicyclic compounds in which Z' is represented by the general formulae:

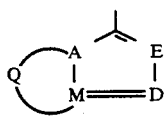
(XIXa)

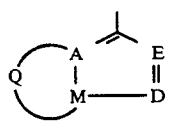
(XIXb)

wherein A, M, D and E each signify a carbon or nitrogen atom and, insofar as they are not bridgehead atoms, carbon atoms are optionally substituted by oxygen, lower alkyl, lower alkoxy, aryl, aralkyl or aryloxy and nitrogen atoms optionally by lower alkyl, aralkyl or aryl, Q is an unsaturated hydrocarbon chain containing 3 to 5 members which is optionally interrupted by nitrogen or sulphur atoms or contains such heteroatoms at the beginning or end of the chain, carbon atoms optionally being substituted by lower alkyl, lower alkoxy, aralkyl, aryloxy or aryl and/or nitrogen atoms optionally by lower alkyl, aralkyl or aryl and two adjacent lower alkyl radicals optionally form a saturated alkylene radical containing 3 to 5 carbon atoms, the sum of the heteroatoms in the bicyclic radical being at most 3, the double bonds of the unsaturated chain Q are in conjugation with the double bond system of the five-membered ring and/or when A or M is a nitrogen atom, this forms enamine structures which belong to both ring systems.

As radicals Z', there are especially preferred the following:

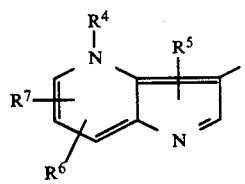
(XX)

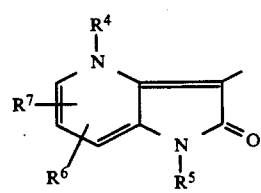
(XXI)

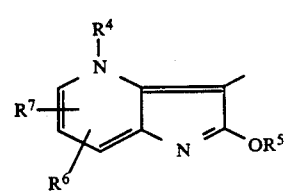
(XXII)

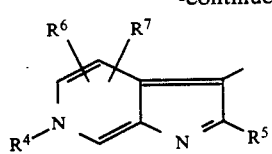
(XXIII)

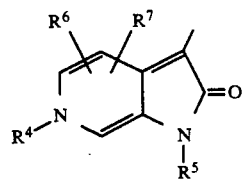
(XXIV)

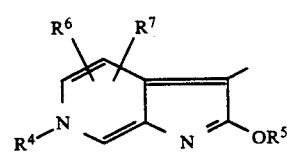
(XXV)

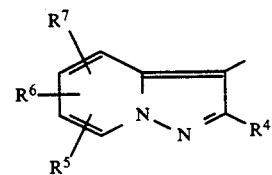
(XXVI)

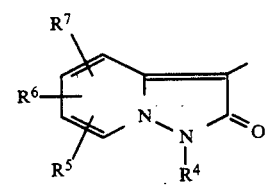
(XXVII)

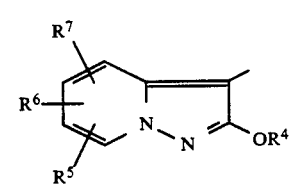
(XXVIII)

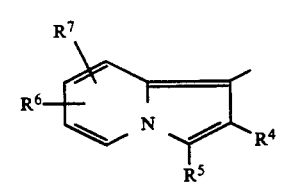
(XXIX)

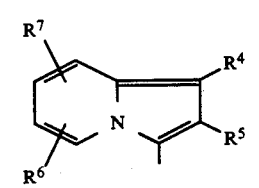
(XXX)

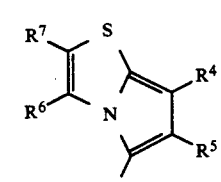
(XXXI)

-continued

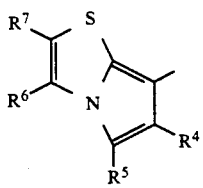 (XXXII)

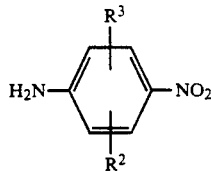 (XXXIV)

those of general formulae XXI, XXIV, XXVII, XXVIII, XXX and XXXI being quite especially preferred.

The meanings of the radicals, A, M, D, E, Q and $R^1$–$R^7$ in the definitions of the general formulae XVII and XIX a/b to XXXII correspond to those given for general formulae II to XVI. This includes the possible amino protective groups of the amino acid or oligopeptide radical $R^1$. Such protective groups, as well as the splitting off thereof, are described, for example, in Houben-Weyl, Volume 15/1.

Bicyclic radicals of the general formula XVIII or those in which Z' has the meaning given in general formulae XIXa) and b) are known or can be prepared analogously to known compounds. Surveys for the synthesis are contained, for example, in "Heterocyclic Compounds", A. Weissberger & E. C. Taylor eds., Volumes 30 and 46; Adv. Heterocyclic Chem., Volume 33, page 185 et seq., 1983; Bull. Chem. Soc. Jap., 49, 1980/1976; and J. Chem. Soc. Perkin I, 1531/1974.

The nitroso compounds of general formula XVII are also new. As intermediates for the preparation of the compounds of general formula II according to the present invention, they are also the subject of the present invention.

They can be obtained by reacting an amino acid or oligopeptide of the general formula:

$$R^1\text{—OH} \qquad \text{(Ia)}$$

in which $R^1$ is an amino acid residue or a residue of an oligopeptide, in which the amino groups are substituted by protective groups, with a) a phenylenediamine derivative of the general formula:

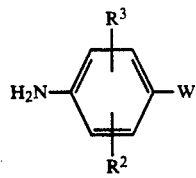 (XXXIII)

wherein $R^2$ and $R^3$, which are the same or different, are hydrogen atoms or lower alkyl, lower alkoxy, carboxyl or lower alkoxycarbonyl radicals or carboxamido groups optionally substituted by lower alkyl or, if $R^2$ and $R^3$ are adjacent, a —CH=CH—CH=CH— radical and W is an amino group substituted by a protective group, subsequently splitting off the amino protective group of the radical W and oxidising the compound with free NH$_2$ groups resulting herefrom, or with b) a p-nitroaniline of the general formula:

wherein $R^2$ and $R^3$ have the same meanings as in general formula XXXIII, reducing the nitro compound resulting herefrom to the corresponding hydroxylamine and then oxidising this.

The nitro compounds prepared according to variant b) by reaction of compounds of general formulae Ia and XXXIV can, of course, also be reduced to the corresponding amino compounds. These are then identical with the phenylenediamine derivatives with a free NH$_2$ group obtained according to variant a) by the reaction of compounds of general formulae Ia and XXXIII, as well as subsequent protective group removal and, like these, can be oxidised to nitroso derivatives of general formula XVII.

The meanings of the radicals $R^1$–$R^3$ given in the compounds of general formulae Ia and XXXIII, as well as XXXIV, correspond to those given in general formula II. The same also applies to the amino protective groups of the protected amino radical W which correspond to those of the amino acid or oligopeptide residue $R^1$. However, the amino protective groups in $R^1$ and W have not to be the same within the molecules prepared according to variant a).

Condensation reactions between amino acids or oligopeptides and aniline derivatives which are analogous to those of general formulae XXXIII and XXXIV are known from the prior art. Thus, for example detailed surveys are given in Houben-Weyl, Volume 15/1 and Volume 15/3.

The splitting off of the amino protective groups from W takes place analogously to the manner described in Houben-Weyl, Volume 15/1.

The compounds with free amino groups obtained according to variant a) after splitting off the amino protective group can be oxidised analogously to known methods, for example as described in Houben-Weyl, Vol. 10/1, pp. 1017 et seq., and converted into nitroso compounds of general formula XVII. As oxidation agent herefor, it is preferred to use Caro's acid or a peroxy-carboxylic acid, for example peracetic acid.

From Houben-Weyl, Volume 10/1, page 1091 et seq. are known processes for the reduction of nitro compounds to hydroxylamines. These can be carried out analogously to the reduction of the condensation products prepared according to variant b) from compounds of general formulae Ia and XXXIV.

The oxidation of so prepared hydroxylamine derivatives can then take place with strong oxidation agents, chromic acid or sodium periodate being especially preferred for this purpose.

The conversion of nitro compounds prepared according to variant b) into compounds with free NH$_2$ groups prepared according to variant a) can also take place analogously to known methods, for example by reduction with sodium dithionite or by hydrogenation over an appropriate catalyst, for example palladium/charcoal.

The substrates of general formula II according to the present invention are preferably present in the salt form.

They are so prepared and also characterized in this form by a good storage stability. However, with the use of bases, they can easily be converted into the free, neutral, uncharged form.

The free form can be represented by the general formula:

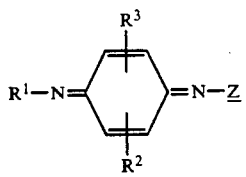
(II')

wherein $R^1$-$R^3$ have the same meanings as in general formula II and Z is an uncharged mesomer of the conjugated-through, positively charged, bicyclic, heterocyclic system Z.

In the case of the synthesis of compounds of general formula II, there are obtained compounds from which, by enzymatic hydrolysis with the help of corresponding peptide bond-cleaving enzymes, there are liberated phenylenediamine derivatives which absorb light at wavelengths of above 420 nm. Generally, the enzymatically liberated coloured materials are red to blue coloured.

In comparison with the previously known substrates for the determination of peptide bond-cleaving enzymes, the compounds according to the present invention possess very advantageous properties. They are water-soluble, stable compounds which can be used not only in wet but also in dry tests.

On the basis of the longwaved light absorption of the phenylenediamine derivatives liberated by enzymatic hydrolysis, disturbances due to the inherent color of sera or due to turbidities are avoided.

Measurement of the intensity of the light absorption of the colored materials liberated by the hydrolysis of the amide bond makes it possible to measure hydrolysis reactions quite exactly. This is because of the difference between the maximum absorption wavelengths of the compounds of formula II, before and the maximum absorption wavelength of the colored material after enzymatic cleavage (i.e., the "λ shift").

Since, in the case of the action of peptide bond-cleaving enzymes on compounds of the general formula II, compounds are directly formed which can be directly determined photometrically and without subsequent reactions, the problem of the disturbance of the enzymatic reaction by the adding of further reaction components, for example of oxidation agents and coupling components for oxidative coupling reactions, is not present. In this regard, the determination of peptide bond-cleaving enzymes can be carried out free of disturbances.

The present invention is also concerned with the use of compounds of general formula II for the detection and determination of the activity of appropriate peptide bond-cleaving enzymes. We have found that the new substrates can be used for the determination of the activity of peptide bond-cleaving enzymes, especially of transpeptidases, peptidases and proteinases. For example, transpeptidases, such as γ-glutamyl transpeptidase, peptidases, such as leucine arylamidase and aminopeptidase M proteinases, such as cathepsins, chymotrypsin, collagenases, elastases, subtilisin, enterokinases, papain, trypsin and especially all proteases which participate in the course of blood coagulation or fibrinolysis can be detected and determined. In particular, the compounds according to the present invention have proved to be especially useful for the determination of γ-glutamyl transpeptidase and leucine arylamidase and of the enzymes which participate in the course of blood coagulation and fibrinolysis, as well as of trypsin and chymotrypsin.

For the detection of such enzymes, compounds of the general formula II are preferably used in which Z has the meaning given in general formula III. Those compounds according to the present invention are especially preferred in which Z has the meanings given in general formulae IV-XVI. Of these, the radicals of general formulae V, VIII, XI, XII, XIV and XV are especially preferred.

Amino acids or amino acid sequences in the meaning of the radical $R^1$ of the compounds of general formula II, which are necessary for the specificity of the substrates according to the present invention for particular enzymes, are known. They can be chosen depending upon the enzyme to be determined. As examples there may be cited the γ-glutamyl radical for γ-glutamyl transpeptidase; the leucine radical for peptidases, such as leucine aminopeptidase; the N-terminal protected tetrapeptide Ile-Glu-Gly-Arg for proteinases, such as trypsin; the N-terminal protected tripeptides Val-Pro-Arg and Gly-Pro-Arg for proteases which participate in the processes of blood coagulation, such as thrombin. Other appropriate amino acids or amino acid sequences are cited in:

Bergmeyer, "Methods of Enzymatic Analysis", 3rd edition, Volume III, pages 349-364, Verlag Chemie, Weinheim, 1983, Z. Klin. Chemie and Klin. Biochem. 10, 192 (1972), Bergmeyer, "Methods of Enzymatic Analysis", 3rd edition, Volume V, pages 124-129, Verlag Chemie, Weinheim, 1984, Seminars in Thrombosis and Hemostasis, Volume 9, Number 3, pages 179-183 (1983), IUPAC Enzyme Nomenclature, 1984, Academic Press, Orlando, T. E. Barman, "Enzyme Handbook", 1969, Supplement I, 1974, Springer Verlag, Heidelberg.

The compounds according to the present invention are then preferably to be used when the activity of enzymes is to be determined photometrically by kinetic or end point processes. For this purpose, one or more of the new substrates, as well as possibly further reagents and adjuvants, are mixed with the sample which contains the enzyme to be determined. The compounds of the general formula II are hydrolysed in the presence of an appropriate peptide bond-cleaving enzyme and a colourforming phenylenediamine derivative is liberated, the change of the absorption of the reaction mixture hereby brought about being measured photometrically. By direct comparison with a standard solution or by indirect comparison with a standard curve, the activity of the enzyme to be determined in the sample can be obtained.

The new substrates can, for example, also be used in blood coagulation tests in which either the activity of coagulation factors is determined via the measurement of their enzyme activity or, in the case of global tests, the time is measured which passes from the start of the reaction up to the formation of a certain enzyme activity. The latter is, for example, the case in the prothrombin time measurement and in the determination of the activated partial thromboplastin time.

In both cases, the speed of the formation of a certain amount of colored material by cleavage of the resulting thrombin is used as measurement value.

The present invention also provides diagnostic agents for the detection and determination of peptide bond-cleaving enzymes. Such diagnostic agents contain at least one of the substrates of general formula II according to the present invention and an appropriate buffer system, as well as possibly further appropriate additional materials usually employed for such diagnostic agents, for example wetting agents, stabilizers and the like. The diagnostic agent can be in the form of a solution, lyophilizate, powder mixture or reagent tablet or can be applied to an appropriate carrier material.

The diagnostic agent according to the present invention in the form of a solution preferably contains all the reagents needed for the enzymatic test. The solvent can be water or a mixture of water with a water-soluble organic solvent, for example methanol, ethanol, acetone or dimethylformamide. For reasons of storage stability, it can be advantageous to divide the reagents needed for the test into two or more solutions which are first mixed when carrying out the actual investigation.

For the preparation of the diagnostic agent in the form of a lyophilizate with a total weight of 5 to 20 mg. and preferably of about 10 mg., a solution is dried which contains all the reagents needed for the test.

A diagnostic agent in the form of a powder mixture or reagent tablet can be prepared by mixing the components of the test with conventional galenical additive materials and granulating. Additive materials of this kind include, for example, sugar alcohols, such as mannitol, sorbitol and xylitol, and other soluble inert compounds, such as polyethylene glycols or polyvinylpyrrolidone. In general, the powder mixtures or reagent tablets have an end weight of about 30 to 200 mg. and preferably of 50 to 80 mg.

For the preparation of a diagnostic agent in the form of a test strip, an absorbent or swellable carrier, preferably filter paper, cellulose or synthetic resin fibre fleece, can be impregnated with solutions of the necessary reagents usually employed for the production of test strips in a readily volatile solvent, for example water, methanol, ethanol or acetone. This can take place in one impregnation step. However, it is often desirable to carry out the impregnation in several steps, solutions thereby being used which, in each case, only contain a part of the components of the diagnostic agent. Thus, for example, in a first step, impregnation can be carried out with an aqueous solution which contains a buffer and other water-soluble additive materials and then, in a second step, with a solution which contains the substrate for the peptide bond-cleaving enzyme. The finished test papers can be used as such or stuck in known manner on to handles or preferably sealed between synthetic resins and fine meshworks according to Federal Republic of Germany Patent Specification No. 21 18 455.

Substrates according to the present invention for the determination of peptide bond-cleaving enzymes and especially of coagulation parameters can also be used in diagnostic agents according to European Patent Specification No. 0 208 218 or Federal Republic of Germany Patent Specification No. 36 10 429 or in agents analogous to those described in European Patent Specification No. 0 045 476, to which reference is hereby made.

The following Examples illustrate some of the numerous process variants which can be used for the synthesis of the compounds according to the present invention, as well as, by way of example, the use of the new substrates for the determination of peptide bond-cleaving enzymes.

The following abbreviations are used in the

EXAMPLES:

Ala=alanine
Arg=arginine
BOC=tert.-butoxycarbonyl
M.p.=melting point
$\gamma$-Glu=$\gamma$-glutamic acid
Gly=glycine
Nle=norleucine
Phe=phenylalanine
Pro=proline
Tos=p-toluenesulphonyl
Hepes=4-(2-hydroxyethyl)-1-piperazine-ethanesulphonic acid
tris=tris-(hydroxymethyl)-aminomethane The given $R_f$ values were determined by thin layer chromatography on silica plates.

EXAMPLE 1

Preparation of 2H-1,4-dihydro-4-methyl-2-oxo-3-(4-tosylglycyl-L-prolyl-L-arginylamido)-phenylimino)pyrrolo[3,2-b]pyridinium sulphate a) 5.7 g. of the triple salt of the approximate formula 2 $KHSO_5 \times K_2SO_4 \times KHSO_4$ (Caroat®, Degussa, Hanau, Germany) are dissolved in 150 ml. of water and the solution adjusted to pH 7 by the addition of potassium carbonate. This solution is added dropwise to a solution of 3.94 g. tosylglycyl-L-prolyl-L-arginine 4-aminoanilide in 210 ml. of water, the mixture is stirred for about a further 5 minutes and the precipitate is filtered off. For purification, the precipitate is dissolved in glacial acetic acid, filtered off from undissolved brown precipitate and the filtrate added dropwise into diethyl ether, with stirring. The precipitated, yellow-brown precipitate is filtered off to give 3 g. (81% of theory) of tosylglycyl-L-prolyl-L-arginyl 4-nitrosoanilide hemisulphate. $R_f$=0.65, n-butanolglacial acetic acid-water (2:1:1 v/v/v).

b) Analogously to the corresponding ethyl ester, the synthesis of which is described in J. Chem. Soc. Perkin I, 1531/1974, there is prepared methyl 2,4-dihydro-2-hydroxypyrrolo-(3,2-b)-pyridine-3-carboxylate (m.p. 270° C. (decomp.)). 6.27 g. of this methyl ester are suspended in 100 ml. dimethylformamide and mixed with 2.1 ml. methyl iodide. While stirring, 1.43 g. of 55% sodium hydride in mineral oil is added portionwise thereto and the mixture subsequently stirred for 2 hours at ambient temperature. The reaction mixture is evaporated and chromatographed on silica gel with acetone/methanol (90:10 v/v), methanol and methanol/water (80:20 v/v). There are obtained 6 g. (88% of theory) methyl 4H-2-hydroxy-4-methylpyrrolo-(3,2-b)-pyridine-3-carboxylate; m.p. 175° C.

0.5 g. of the above-obtained ester is boiled under reflux with 30 ml. concentrated hydrochloric acid for 2 hours. The reaction mixture is evaporated, the residue is dissolved in methanol and the product is precipitated out by the addition of diethyl ether to give 0.3 g. (84% of theory) 2H-1,4-dihydro-4-methylpyrrolo-(3,2-b)-pyridin-2-one; m.p. 220° C.

c) 0.684 g. of the nitroso compound obtained in Example 1a) is dissolved in 7 ml. glacial acetic acid and mixed dropwise, while stirring, with a solution of 0.148 g. 2H-1,4-dihydro-4-methylpyrrolo-(3,2-b)-pyridin-2-one from Example 1b) in 6 ml. dimethylformamide. The red solution is stirred for 8 hours at ambient temperature, stored overnight in a refrigerator, evaporated and the residue chromatographed on a silica gel column with n-butanol/glacial acetic acid/water (2:1:1 v/v/v). The product-containing fractions are combined and evaporated. The residue is digested with diethyl ether and filtered off with suction to give 0.17 g. of a red compound of the following structure:

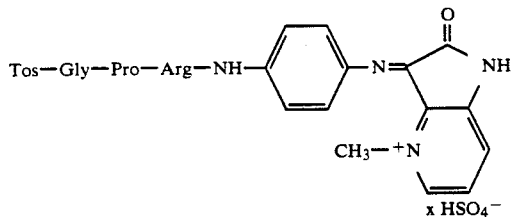

$R_f$=0.18 (n-butanol-glacial acetic acid-water (2:1:1 v/v/v); m.p. 167°–170° C.

EXAMPLE 2

Analogously to Example 1, by the reaction of tosyl-glycyl-L-prolyl-L-arginine-4-nitrosoanilide and the heterocyclic compounds set out in the following Table 1, there are obtained the following chromogenic peptide hydrolase substrates:

R = Tos—Gly—Pro—Arg—NH—⟨phenyl⟩—

| Example No. | structure of the chromogenic substrate | $R_f^{1)}$ value | m.p. | structure of the starting heterocycle |
|---|---|---|---|---|
| 2a) | [R—N=pyrazolo-pyridinium, OCH₃, HSO₄⁻] | 0.31 | 190° C. (decomp.) | [pyrazolo[1,5-a]pyridine-OCH₃] |
| 2b) | [R—N= structure with N—CH₃, N⁺, HSO₄⁻] | 0.22 | 163° C. (decomp.) | [pyrazolopyridinone N—CH₃] |
| 2c) | [R—N= structure with N—CH₃, CH₃—N⁺, HSO₄⁻] | 0.11 | 181° C. (decomp.) | [CH₃—N pyrrolopyridinone N—CH₃] |

-continued
R = Tos—Gly—Pro—Arg—NH—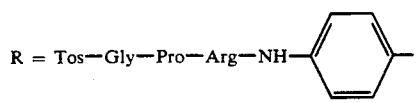
| Example No. | structure of the chromogenic substrate | $R_f$[1] value | m.p. | structure of the starting heterocycle |
|---|---|---|---|---|
| 2d) | | 0.33 | 47° C. (decomp.) | |
| 2e) | | 0.18 | 220° C. (decomp.) | |
| 2f) | | 0.59 | 165° C. (decomp.) | |
| 2g) | | 0.15 | 135° C. | |
| 2h) | | 0.44 | 168° C. (decomp.) | |

-continued

R = Tos—Gly—Pro—Arg—NH—⟨phenyl⟩

| Example No. | structure of the chromogenic substrate | R_f 1) value | m.p. | structure of the starting heterocycle |
|---|---|---|---|---|
| 2i) | [structure with CH₃, C₂H₅, R—N=, +N, S, cyclohexane ring; HSO₄⁻] | 0.50 | 170° C. (decomp.) | [structure with CH₃, C₂H₅, N, S, cyclohexane ring] |
| 2k) | [structure with R—N=, C=O, N—CH₃, CH₃—N⁺, CH₃O; HSO₄⁻] | 0.52 | 171° C. (decomp.) | [structure with C=O, N—CH₃, CH₃N, CH₃O] |

1) silica gel, elution agent n-butanol/glacial acetic acid/water 2:1:1 (v/v/v)

Preparation of the starting heterocycle for Example 2c)

5 g. Ethyl 2,3-dihydro-2-hydroxypyrrolo-(3,2-b)-pyridinecarboxylate are suspended in 180 ml. dimethylformamide. To this are added 10 ml. methyl iodide and subsequently portionwise 4 g. sodium hydride (55%). The reaction mixture is stirred for 3 hours at ambient temperature and evaporated. The residue is dissolved in water and the solution is extracted several times with methylene chloride. The combined organic phases are dried and evaporated, the residue is dissolved in a little hot acetone and the product is precipitated out with diethyl ether to give 3.2 g. of the corresponding N,N'-dimethyl compound (m.p. 145°–147° C.) which is boiled under reflux with 110 ml. concentrated hydrochloric acid for 24 hours. The reaction mixture is evaporated to dryness, dissolved in water and the solution rendered alkaline by the addition of sodium carbonate. It is extracted several times with methylene chloride and the organic phases are combined and evaporated to give 1.9 g. (90% of theory) 2H-1,4-dihydro-1,4-dimethylpyrrolo-(3,2-b)-pyridin-2-one, m.p. 144° C.

Preparation of the starting heterocycle for Example 2d)

Analogously to the preparation of the starting heterocycle for Example 2c), from ethyl 2,3-dihydro-2-hydroxypyrrolo(2,3-c)-pyridine-3-carboxylate there is obtained 2H-1,6-dihydro-1,6-dimethylpyrrolo-(2,3-c)-pyridin-2-one. The crude product is chromatographed on silica gel with methylene chloride/methanol (9:1 v/v) to give a yellow, amorphous substance.

R_f=0.46 (methylene chloride/methanol (9/1 v/v))

Preparation of the starting heterocycle for Example 2g)

Analogously to the preparation of the starting heterocycle for Example 2 c), from ethyl 2,3-dihydro-5-methyl-2-hydroxypyrrolo-(3,2-b)-pyridine-3-carboxylate (m.p. 252° C.; prepared analogously to the 5-H compound, J. Chem. Soc. Perkin I, 1521/1974) there is obtained the N,N'-dimethyl compound 2H-1,4-dihydro-1,4,5-trimethylpyrrolo-(3,2-b)-pyridin-2-one; m.p. 195°–200° C.

Preparation of the starting heterocycle for Example 2h)

Analogously to the preparation of the starting heterocycle for Example 2c), by alkylation with n-propyl iodide with subsequent saponification and decarboxylation of the ethyl carboxylate, there is obtained 2-H-1,4-dihydro-1,4-di-propylpyrrolo-(3,2-b)-pyridin-2-one as an oily product.

R_f=0.4 (ethyl acetate/ethanol (9:1 v/v)).

Preparation of the starting heterocycle for Example 2i)

10.5 g. Butyric acid amide and 5.4 g. phosphorus pentasulphide are suspended in 8 ml. toluene and, first with cooling and then at about 75° to 80° C., mixed with a solution of 21.5 g. 2-bromocyclohexanone in 10 ml. toluene. The reaction mixture is then heated under reflux for 15 minutes, allowed to cool and the pH value of the reaction mixture adjusted to 8 to 9 with a 2N aqueous solution of sodium hydroxide. The product is extracted with ethyl acetate. For purification, the product is distilled (b.p. 77°–84° C./0.1 mm.Hg) and filtered over silica gel with the use of ligroin/ethyl acetate (10:1 v/v) to give 3.1 g. 2-n-propyl-4,5,6,7-tetrahydrobenzo-1,3-thiazole; R_f=0.35, ligroin/ethyl acetate 90:10 v/v). 2.7 g. of this compound are dissolved in 25 ml. acetone, mixed with 3.06 g. bromoacetone and heated under reflux for 14 hours. The acetone is distilled off and the residue is mixed with 335 ml. ethanol and 8.7 g. sodium ethylate. The reaction mixture is heated under reflux for 1 hour and evaporated to about 50 ml. The solution is poured into 500 ml. water and extracted with ethyl acetate. The crude product is chromatographed with ligroin/ethyl acetate (98:2 v/v) over silica gel. There is obtained 1 g. of the desired pyrrolo-[2,1-b]thiazole of the following structure (m/e=219):

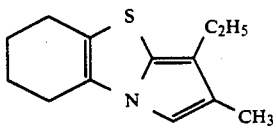

Preparation of the starting heterocycle for Example 2k)

48.5 ml. diethyl malonate are added at about 80° C. to a suspension of potassium butylate (prepared from 12.48 g. potassium and 600 ml. tert.-butanol). To the white suspension obtained is added dropwise a hot solution of 30.2 g. 2-chloro-6-methoxy-3-nitropyridine in 200 ml. tert.-butanol. The reaction mixture is heated under reflux for 17 hours, then evaporated to dryness and the residue suspended in water, neutralized with 2N hydrochloric acid and extracted repeatedly with diethyl ether. The dried ethereal phase is evaporated and the residue purified by chromatography on silica gel with ethyl acetate/ligroin (1:9 v/v). There is obtained 40.4 g. (81% of theory) diethyl 2-(6-methoxy-3-nitro)pyridylmalonate; m.p. 84°-85° C.

20 g. of the product obtained are dissolved in 500 ml. ethanol/methylene chloride (4:1 v/v) and hydrogenated in the presence of a palladium/charcoal catalyst. The catalyst is filtered off and the filtrate is concentrated to about 250 ml. and mixed with 25 ml. glacial acetic acid. The mixture is heated under reflux for 4 hours and then left to stand overnight in a refrigerator. The precipitate formed is filtered off. From the mother liquor there is obtained a further amount of product by concentration to about 100 ml. and mixing with about 500 ml. diethyl ether. In total, the yield of ethyl 1,4-dihydro-2-hydroxy-5-methoxypyrrolo-[3,2-b]-pyridine-3-carboxylate is 10.8 g. (72% of theory); m.p. 184°-186° C.

Analogously to the preparation of the starting heterocycle for Example 2c), from the above-described compound there is obtained 2H-1,4-dihydro-1,4-dimethyl-5-methoxypyrrolo-[3,2-b]-pyridin-2-one; m.p. 156°-159° C.

EXAMPLE 3

Preparation of 2H-1,4-dihydro-4-benzyl-2-oxo-3-(4-N-methoxycarbonyl-N-norleucyl-glycyl-L-arginylamido)phenylimino)-pyrrol-[3,2-b]-pyridinium sulphate 0.95 g. N-methoxycarbonyl-D-norleucyl-glycyl-L-arginine-4-nitroanilide acetate are dissolved in a mixture of 20 ml. ethanol, 10 ml. water and 1 drop glacial acetic acid and hydrogenated over palladium/charcoal. The mixture is evaporated, dissolved in 300 ml. of water and freeze dried to give 0.89 g. (100% of theory) N-methoxycarbonyl-D-norleucyl-glycyl-L-arginine-(4-aminoanilide) acetate; m.p. 108° C.

This compound is converted into the nitroso compound analogously to Example 1a) and reacted analogously to Example 1c) with 2H-1,4-dihydro-4-benzyl-pyrrolo-(3,2-b)-pyridin-2-one to give the chromogenic peptide hydrolase substrate of the following structure.

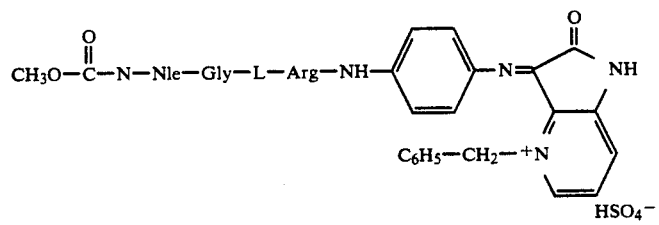

M.p. 95°-97° C.; $R_f$=0.08 (ethyl acetate/acetone/glacial acetic acid/water 50:25:12.5:12.5 v/v/v/v).

EXAMPLE 4

Preparation of 2H-1,4-dihydro-1,4-dimethyl-2-oxo-3-(4-(L-γ-glutamylamido)-phenylimino)-pyrrolo-[3,2-b]-pyridinium bis-trifluoroacetate.

a) 2.85 g. L-γ-Glu-p-nitroanilide hydrate are suspended in 25 ml. dioxan and mixed with 1.15 g. 1,1,3,3-tetramethylguanidine and 25 ml. water. To this is added a solution of 2.4 g. di-tert.-butyl dicarbonate in 4 ml. dioxan and the reaction mixture is stirred for 4 hours at ambient temperature. The reaction mixture is then mixed with water and extracted with diethyl ether. The aqueous phase is adjusted to pH 3 by the addition of 2N hydrochloric acid and extracted with ethyl acetate. The organic phase is dried and evaporated. The residue becomes crystalline by the addition of ligroin. There are obtained 3.3 g. BOC-L-γ-Glu-p-nitroanilide which is dissolved in a mixture of 150 ml. ethanol and 50 ml. water and hydrogenated in the presence of palladium/charcoal. After filtering off the catalyst and evaporating the filtrate, there are obtained 2.99 g. (88% of theory) BOC-L-γ-Glu-(4-aminoanilide).

b) 2.47 g. of the compound obtained in Example 4a) are dissolved in 70 ml. of a 2.5% aqueous solution of sodium bicarbonate and mixed, while stirring, with a solution of 500 mg. of the triple salt 2KHSO₅×KHSO₄×K₂SO₄ (Caroat ®, Degussa, Hanau, Germany) in 2 ml. water. After stirring for two hours at ambient temperature, the reaction mixture is acidified with glacial acetic acid and extracted with ethyl acetate. The organic phase is dried and evaporated to give 1.95 g. (76% of theory) BOC-L-γ-Glu-(4-nitrosoanilide).

$R_f$=0.8 (acetone/methylene chloride/glacial acetic acid 50:45:5 v/v/v).

c) 1.9 g. of the nitroso compound obtained in Example 4b) is dissolved in 70 ml. glacial acetic acid and mixed with 0.8 g. 2H-1,4-dihydro-1,4-dimethylpyrrolo-(3,2-b)-pyridin-2-one. The mixture is stirred for 2 hours at ambient temperature and the product precipitated out by the addition of diethyl ether and filtered off. The crude product is purified by chromatography on silica gel with methanol and methanol/water (90:10 v/v) as eluent. The product-containing fractions are combined and evaporated to give 0.74 g. (25% of theory) of a compound of the following structure:

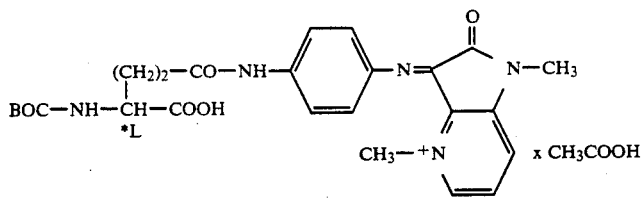

$R_f$=0.15 (methanol/water 9:1 v/v).

d) 0.64 g. of the compound obtained in Example 4c) is dissolved in 10 ml. trifluoroacetic acid and, after 30 minutes, the solution is evaporated to dryness. The residue is recrystallised from methanol/diethyl ether to give 0.7 g. (100% of theory) of a compound of the following structure:

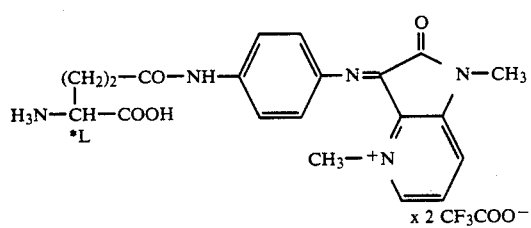

M.p. 167° C.; $R_f$=0.1 (n-butanol/glacial acetic acid/water 2:1:1 v/v/v).

EXAMPLE 5

Preparation of
2H-1,4-dihydro-1,4-dimethyl-2-oxo-3-(4-N-succinyl-L-phenylalanylamido)-phenylimino)-pyrrolo-[3,2-b]-pyridinium hemisulphate 10 g. N-succinyl-L-phenylalanine-p-nitroanilide are hydrogenated in a mixture of 300 ml. ethanol and 100 ml. water in the presence of palladium/charcoal to give 9.2 g. (99% of theory) N-succinyl-L-phenylalanine 4-aminoanilide; m.p. 167°-168° C. (decomp.). Analogously to Example 4c), this compound is converted into the chromogenic substrate of the following structure:

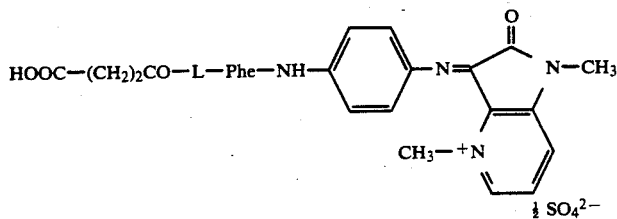

M.p. 158°-162° C. (decomp.); $R_f$=0.2 (ethyl acetate/acetone/glacial acetic acid/water 50:25:12.5:12.5 v/v/v/v).

EXAMPLE 6

Preparation of
1,2-dimethyl-5-ethyl-3-(4-(N-succinyl-L-phenylalanylamido)-phenylimino)-indolizinium hemisulphate.

The nitroso compound obtained in Example 5 is reacted analogously to Example 4c) with 1,2-dimethyl-5-ethylindolizine, the nitroso compound being used in 1.4 fold excess and the reaction time being limited to 15 minutes, to give a compound of the following structure:

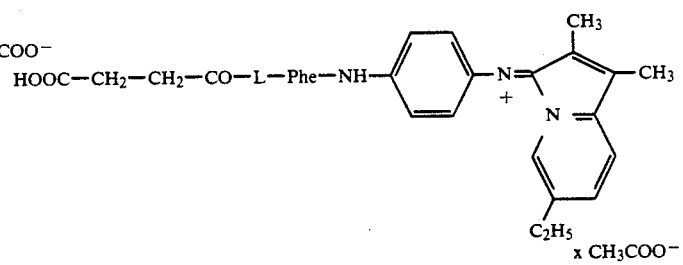

which is purified by chromatography on silica gel with methanol/water (90:10 v/v) as elution agent; m.p. 125°-130° C. (decomp.); $R_f$=0.25 ethyl acetate/acetone/glacial acetic acid/water (50:25:12.5:12.5 v/v/v/v).

EXAMPLE 7

Preparation of
1,2-dimethyl-3-(4-(N-tert.-butoxycarbonyl-L-alanylamido)-2-methoxyphenylimino)indolizinium acetate a) 50 g. 2-methoxy-4-nitroaniline are dissolved in 820 ml. ethyl acetate and mixed with 70.45 g. benzyl chloroformate. The mixture is heated under reflux for 5 hours, cooled and the precipitated crystals filtered off to give 54.6 g. (61% of theory) N-benzyloxycarbonyl-2-methoxy-4-nitroaniline which is dissolved in a mixture of 500 ml. tetrahydrofuran and 500 ml. water and, while cooling, mixed portionwise with 210 g. sodium dithionite. After the completed reduction the mixture is diluted with 500 ml. water and extracted with ethyl acetate.

The extract is dried with anhydrous sodium sulphate and molecular sieve and evaporated to give 26.8 g. (59% of theory) 4-benzyloxycarbonylamindo-3-methoxyaniline; m.p. 65°-68° C.

b) 1.89 g. BOC-L-alanine is dissolved in 40 ml. tetrahydrofuran and mixed with 1.1 ml. N-methylmorpholine. At −15° C., 1.31 ml. isobutyl chloroformate is added dropwise thereto. After 15 minutes at −15° C., there is added thereto a solution of 2.75 g. of the compound obtained in Example 7a) in 10 ml. tetrahydrofuran. The reaction mixture is stirred for 15 minutes at −15° C. and for 1 hour at −10° C. and finally allowed to warm up to ambient temperature. The reaction mixture is evaporated and the residue is taken up in ethyl acetate and shaken up with 5% aqueous solution of sodium bicarbonate. The organic phase is dried and evaporated. The crude product obtained is recrystallised from ethanol to give 2.58 g. (58% of theory) BOC-L-Ala-(4-benzyloxycarboxamido-3-methoxyanilide); m.p. 144°-145° C.

c) 2.55 g. of the compound obtained in Example 7b) are dissolved in 70 ml. dimethylformamide and hydrogenated in the presence of palladium/charcoal. The catalyst is filtered off and the filtrate evaporated to give 1.72 g. (97% of theory) BOC-L-Ala-(4-amino-3-methoxyanilide); m.p. 115°-129° C.

d) Analogously to Example 4b), the above-obtained compound is oxidized to the nitroso compound and reacted analogously to Example 4c) with 1,2-dimethylindolizine, the nitroso compound being used in 1.4 fold excess and the reaction time being limited to 15 minutes. There is obtained a compound of the following structure:

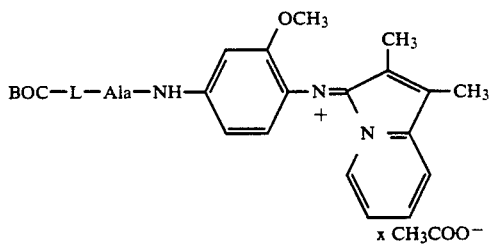

which is purified by chromatography on silica gel with ethyl acetate/acetone/glacial acetic acid/water (50:25:12.5:12.5 v/v/v/v) as elution agent.

$R_f$=0.28 (ethyl acetate:acetone:glacial acetic acid: water 50:25:12.5:12.5 v/v/v/v)

$R_f$=0.58 (n-butanol/glacial acetic acid/water 2:1:1 v/v/v).

EXAMPLE 8

Preparation of 1,2-dimethyl-3-(4-(L-alanylamido)-2-methoxyphenylimino)-indolizinium trifluoroacetate The compound of Example 7 is treated with trifluoroacetic acid analogously to Example 4d) for splitting off the BOC group. There is obtained a compound of the following structure:

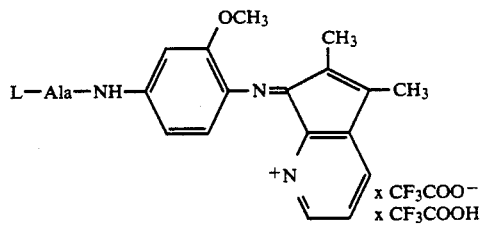

M.p. 78° C. (decomp.); $R_f$=0.15 (n-butanol/glacial acetic acid/water 2:1:1 v/v/v).

EXAMPLE 9

Preparation of 2H-1,4-dihydro-1,4-dimethyl-2-oxo-3-(4-(N-tert.-butoxy-L-alanyl-L-alanylamido)-2-methylphenylimino)pyrrolo-[3,2-b]-pyridinium acetate a) Analogously to Example 7a), from 50 g. 2-methyl-4-nitroaniline is prepared 81.3 g. (88% of theory) N-benzyloxycarbonyl-2-methyl-4-nitroaniline which is reduced with sodium dithionite to give 44 g. 4-benzyloxycarbonylamido-3-methylaniline; m.p. 60°-62° C.

Analogously to Example 7b), 2.6 g. BOC-L-Ala-Ala in dimethylformamide are reacted with the above-obtained p-phenylenediamine derivative. Yield 1.35 g. (27% of theory); m.p. 197°-199° C.

The product obtained is hydrogenated over palladium on charcoal to give 1.19 g BOC-L-Ala-Ala-(4-amino-3-methylanilide); m.p. 135° C.

b) The compound obtained in Example 9a) is oxidized analogously to Example 4b) to the nitroso compound and reacted according to Example 4c) with 4H-1,4-dihydro-1,4-dimethyl-2-oxopyrrolo-(3,2-b)-pyridin-2-one to give a compound of the following structure:

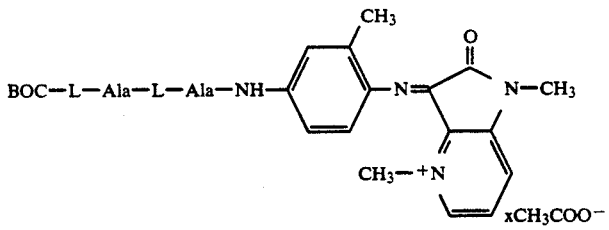

$R_f$=0.2 (ethyl acetate/acetone/glacial acetic acid/water 50:25:12.5:12.5 v/v/v/v).

EXAMPLE 10

Preparation of 2H-1,4-dihydro-1,4-dimethyl-2-oxo-3-(4-(L-alanyl-L-alanylamido)-2-methylphenylimino)-pyrrolo-[3,2-b]-pyridinium bis-trifluoroacetate The compound of Example 9b) is treated with trifluoroacetic acid analogously to Example 4d) for the splitting off of the BOC group. There is obtained a compound of the following structure:

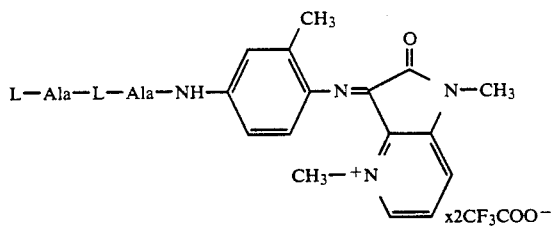

M.p. 127°-132° C. (decomp.);
R_f=0.1 (n-butanol:glacial acetic acid:water 2:1:1 v/v/v).

EXAMPLE 11

Preparation of 3-(4-(D,L-N-benzoylarginylamido)phenylimino)-1-methyl-2-phenylindolizinium sulphate N-Benzoyl-D,L-arginine-4-nitroanilide is hydrogenated analogously to Example 3 in the presence of palladium/charcoal to give the amino compound which is oxidised analogously to Example 1a) to give the nitroso compound is reacted with 1-methyl-2-phenylindolinzine, the nitroso compound being used in twofold excess and the reaction time being limited to 15 minutes. There is obtained the following chromogenic peptide hydrolase substrate:

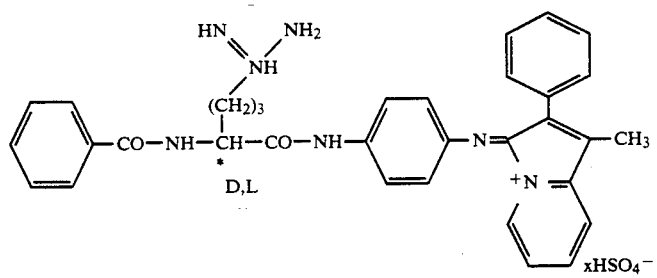

R_f=0.38 (n-butanol/glacial acetic acid/water 2:1:1 v/v/v).

EXAMPLE 12

Preparation of 1,2-diphenyl-3-(4-L-alanylamido)phenyliminoindolizinium trifluoroacetate.

Analogously to Example 7, from BOC-L-alanine, N-carbobenzoxyphenylenediamine and 1,2-diphenylindolizine there is obtained 1,2-diphenyl-3-(4-tert.-butoxycarbonyl-L-alanylamido)-phenylimidoindolizinium acetate. The BOC group is split off analogously to Example 8 to give a compound of the following structure:

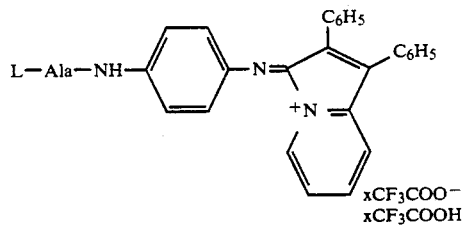

M.p. 114°-116° C. (decomp.); R_f=0.2 (n-butanol/glacial acetic acid/water 2:1:1 v/v/v).

EXAMPLE 13

Preparation of 2H-1,4-dihydro-1,4-dimethyl-2-oxo-3-(4-(L-alanylamido)-2-(N-isopropylamidocarbonyl)-phenylimino)-pyrrolo[3,2-b]-pyridinium bis-trifluoroacetate.

a) 5.46 g. 5-Amino-2-nitrobenzoic acid and 4.6 g. 1-hydroxybenzotriazole hydrate are dissolved in 30 ml. dimethylformamide and the solution mixed at about 10° to 15° C. with a solution of 6.18 g. dicyclohexylcarbodiimide. After 1 hour at ambient temperature, 2.6 ml. isopropylamine are added thereto with slight cooling. The reaction mixture is stirred for a further 2 hours at ambient temperature and, after leaving to stand overnight, is worked up. The precipitate is filtered off and the filtrate is evaporated. The residue is taken up in ethyl acetate and the solution rapidly washed with an aqueous solution of sodium bicarbonate. The precipitate from the ethyl acetate phase is isolated and dried to give 5.5 g. 2-(N-isopropylamidocarbonyl)-4-nitroaniline; m.p. 211° C.

b) 4.4 g. BOC-L-alanine, 5.2 g. of the compound obtained in a) and 1.77 g. imidazole are dissolved in 117 ml. pyridine and mixed at −20° C. with 3.4 ml. phosphorus oxychloride. After the addition, the reaction mixture is slowly warmed up to ambient temperature, the pyridine is distilled off and the residue is taken up in an aqueous solution of sodium bicarbonate and extracted with ethyl acetate. The ethyl acetate extract is washed with aqueous sodium bicarbonate solution and aqueous citric acid solution (5% by weight), dried and evaporated. The crude product is purified by chromatography on silica gel with ligroin-acetone (2:1 v/v) as elution agent. The product fractions are recrystallised from diethyl ether/ligroin. There are obtained 3.2 g. BOC-L-alanyl-2-(N-isopropylamidocarbonyl)-4-nitroanilide; m.p. 125°-129° C. (decomp.).

c) The compound obtained in b) is hydrogenated in 150 ml. ethanol and 50 ml. water in the presence of palladium/charcoal. The reaction product is oxidised analogously to Example 4b) to give the nitroso compound and reacted analogously to Example 4c) with 2H-1,4-dihydro-1,4-dimethylpyrrolo-[3,2-b]-pyridin-2-one. The splitting off of the BOC protective group is carried out analogously to Example 4d) to give the title compound of the following structure:

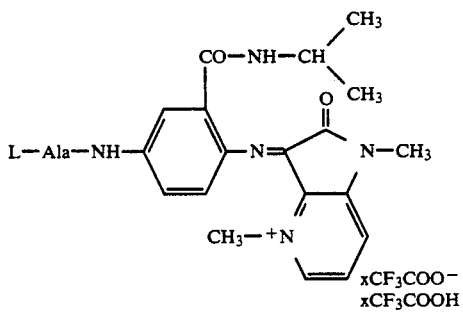

$R_f$=0.1 (n-butanol/glacial acetic acid/water 2:1:1 v/v/v); m.p. 124° C. (decomp.).

EXAMPLE 14

Preparation of 2H-1,4-dihydro-1,4-dimethyl-2-oxo-3-(4-(N-tert.-butoxy-D-phenylalanyl-L-prolyl-L-arginylamido)-phenylimino)-pyrrolo[3,2-b]-pyridinium sulphate.

a) Synthesis of N-carbobenzoxyphenylenediamine.

Analogously to Example 7a), from 60 g. p-nitroaniline and 204 ml. benzyl chloroformate there is obtained a total of 109.9 g. N-benzyloxycarbonyl-4-nitroanilide ($R_f$=0.75; silica gel, toluene-dioxanglacial acetic acid 72:20:8 v/v/v) which is dissolved in 1090 ml. tetrahydrofuran and mixed with 1900 ml. 2N aqueous sodium hydroxide solution and 436 g. sodium dithionite. For completion of the reduction, a solution of 100 g. sodium dithionite in 1000 ml. water is again added thereto. The reaction mixture is diluted with water and the product extracted with ethyl acetate. The crude product is recrystallised from ethyl acetate: ligroin (2:1 v/v). There are obtained 57.3 g. of the title compound. $R_f$=0.3 (silica gel; toluene-dioxanglacial acetic acid 72:20:8 v/v/v).

b) BOC-L-prolyl-(Nω-nitroarginyl)-4-benzyloxycarbonylamidoanilide.

18 g. (443 mMole) BOC-L-Pro-(Nω-nitro-Arg)-OH, 13.15 g. (85.8 mMole) N-hydroxybenzotriazole hydrate and 10.9 g. (45.1 mMole) N-carbobenzoxyphenylenediamine are slowly dissolved in 240 ml. dimethylformamide. The solution is cooled to −10° C. and mixed dropwise with a solution of 9.7 g. (47 mMole) dicyclohexylcarbodiimide in 70 ml. dimethylformamide. Thereafter, the reaction mixture is stirred for 1 hour at 0° C. and subsequently at ambient temperature. After leaving to stand overnight, the dicyclohexylurea is filtered off with suction, the dimethylformamide solution is concentrated to about one half, mixed with about the equal volume of water and the mixture extracted twice with ethyl acetate. The combined extracts are washed with aqueous citric acid solution (5% by weight) or with 5% aqueous potassium hydrogen sulphate solution, water, 5% aqueous sodium bicarbonate solution and water. The ethyl acetate phase is evaporated, the residue is dissolved in acetone and, after standing for some time, residual dicyclohexylurea is filtered off with suction. The filtrate is evaporated and the residue recrystallised from ethyl acetate. The product crystallises very slowly. After standing for 2 to 3 days, the crystals are filtered off with suction. Yield 19.09 g. (69% of theory). For purification, the product is chromatographed over silica gel with methanol.

$R_f$=0.8 (silica gel; acetone/methylene chloride/glacial acetic acid 50:45:5 v/v/v).

c) 24.3 g. of the protected dipeptide obtained in b) are dissolved in 200 ml. tetrahydrofuran and mixed, while stirring, with 200 ml. ethereal hydrochloric acid (about 5N). A sticky precipitate is obtained which crystallises upon stirring at ambient temperature for about 1.5 hours. The precipitate is filtered off with suction, well washed with diethyl ether and dried at 50° C. in a vacuum drying cabinet. There are obtained 22.4 g. (100% of theory) of the title compound.

$R_f$=0.55 (silica gel; ethyl acetate/acetone/glacial acetic acid/water 50:25:12.5:12.5 v/v/v/v).

d) BOC-D-Phenylalanyl-L-prolyl-Nω-nitro-L-arginyl-(4-benzyloxycarbonylanilide).

4.64 g. BOC-D-phenylalanine and 5.05 g. of the compound obtained in c) are dissolved in 52 ml. dimethylformamide and cooled to 0° C. The solution is mixed with 5.25 ml. N-methylmorpholine and 7.7 g. of a 50% by weight solution of n-propanephosphonic acid anhydride in methylene chloride. The reaction mixture is left to stand overnight and then evaporated. The residue is taken up in ethyl acetate and the organic phase is washed with 5% sodium bicarbonate solution, water and 0.5N hydrochloric acid. The organic phase is dried and evaporated, there being obtained 4.92 g. of an oily product.

$R_f$=0.45 (silica gel; methylene chloride-methanol 95:5 v/v).

e) BOC-D-Phenylalanine-L-prolyl-L-arginyl (4-aminoanilide).

9.6 g. of the compound obtained in d) are dissolved in 250 ml. ethanol, 25 ml. water and 15 ml. glacial acetic acid and hydrogenated in the presence of 2.4 g. of palladium/charcoal at about 6 bar. After filtering off the catalyst and evaporating the filtrate, the residue obtained is crystallized with diethyl ether. There are obtained 4.93 g. BOC-D-phenylalanyl-L-prolyl-L-arginyl-(4-aminoanilide); m.p. 133°-135° C. (decomp.);

$R_f$=0.6 (ethyl acetate/acetone/glacial acetic acid/water 50:25:12.5:12.5 v/v/v/v).

f) Analogously to Example 1a), the compound obtained above in e) is oxidised to the nitroso compound and reacted analogously to Example 1c) with 2H-1,4-dihydro-1,4-dimethylpyrrolo-[3,2]-pyridin-2-one. A compound of the following structure is obtained:

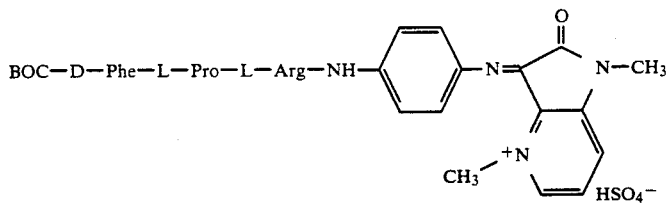

which is purified by chromatography on silica gel with n-butanol/glacial acetic acid/water (2:1:1 v/v/v); m.p. 175° C. (decomp.); $R_f$=0.38 (silica gel; n-butanol/glacial acetic acid/water 2:1:1 v/v/v).

EXAMPLE 15

Preparation of 2H-1,4-dihydro-1,4-dimethyl-2-oxo-3-(4-(D-phenylalanyl-L-prolyl-L-arginylamido)-phenylimino)-pyrrolo-(3,2-b)-pyridinium sulphate trifluoroacetate.

The compound from Example 14 is treated with trifluoroacetic acid analogously to Example 4d) for splitting off the BOC group. There is obtained a compound of the following structure:

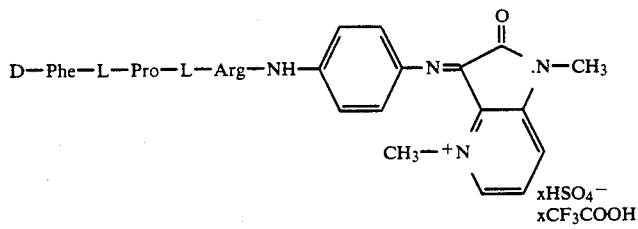

M.p. 185° C. (decomp.); $R_f$=0.15 (n-butanol/glacial acetic acid/water 2:1:1 v/v/v).

EXAMPLE 16

Enzymatic cleavage of the compounds according to the present invention.

By way of example, the detection of peptide bond-cleaving enzymes is shown on the basis of some compounds.

Thrombin

The compound from Example 1c) and the compounds from Examples 2b), 2c), 2d), 2e), 2f), 2g), 2h), 2i), 2k), 14 and 15 were, in each case, dissolved in 0.1 mole/liter of hepes buffer (pH 7.5) and mixed with thrombin.

The absorption maxima for the compounds according to the present invention before and after the cleavage are given in the following summary:

| compound from Example | $\lambda_{max}$ in nm before cleavage | $\lambda_{max}$ in nm after cleavage |
|---|---|---|
| 1c) | 526 | 544 |
| 2a) | 515 | 566 |
| 2b) | 501 | 562 |
| 2c) | 525 | 558 |
| 2d) | 342 with shoulder at 420 | 568 |
| 2e) | 470 | 584 |
| 2f) | 464 | 588 |
| 2g) | 528 | 564 |
| 2h) | 529 | 564 |
| 2i) | 449 | 540 |
| 2k) | 530 | 567 |
| 14) | 525 | 558 |
| 15) | 525 | 558 |

Coagulation factor Xa

The compound of Example 3 was dissolved in 0.1 mole/liter of hepes buffer (pH 7.5) and then reacted with bovine coagulation factor Xa. The measurements gave an absorption maximum of 532 nm before and of 564 nm after the cleavage.

γ-Glutamyltranspeptidase

The substance of Example 4c) was dissolved together with 50 mole/liter glycylglycine in tris buffer (0.1 mole/liter, pH 7.5) and then reacted with γ-glutamyltranspeptidase. The measurements resulted in an absorption maximum of 525 nm before and of 558 nm after the cleavage.

Chymotrypsin

The compounds of Examples 5 and 6 were, in each case, dissolved in 0.2 mole/liter of tris buffer (pH 8.1) and 25 mole/liter sodium chloride solution, with the addition of calcium ions, and reacted with chymotrypsin. The absorption maxima were determined before and after the cleavage.

Compound of Example 5:
 before cleavage 525 nm,
 after cleavage 558 nm.
Compound of Example 6:
 before cleavage 366 nm
 with a shoulder at 485 nm,
 after cleavage 594 nm.

Aminopeptidase M:

The compounds of Examples 8, 10, 12 and 13 were, in each case, dissolved in 0.2 mole/liter of tris buffer (pH 8.1) and reacted with aminopeptidase M. The absorption maxima were determined before and after the cleavage.

| compound from Example | $\lambda_{max}$ in nm before cleavage | $\lambda_{max}$ in nm after cleavage |
|---|---|---|
| 8 | 512 | 558 |
| 10 | 544 | 566 |
| 12 | 446 | 605 |

| 13 | 530 | 567 |

Subtilisin

The compound of Example 9b) was dissolved in 0.2 mole/liter of tris buffer (pH 8.1) and reacted with subtilisin. The measurements gave an absorption maximum of 548 nm before and 566 nm after the cleavage.

Trypsin

The compound of Example 11 was dissolved in 200 mole/liter of tris/HCl (pH 8.1) and reacted with trypsin. The measurements gave before cleavage an absorption maximum at 418 nm with a shoulder at 525 nm and after cleavage an absorption maximum of 594 nm.

EXAMPLE 17

Determination of the prothrombin time

Preparation of the reagent 58 mg. of the compound of Example 2c) are dissolved in 100 ml. 0.1 mole/liter of hepes buffer (pH 7.0) and mixed with 36 ml. thromboplastin prepared according to European Patent Specification No. 0 083 773. The solution is divided up into 3 ml. amounts, placed into 35 ml. bottles and lyophilised.

The lyophilisate of a bottle is dissolved in 30 ml. of 0.1 mole/liter hepes buffer (pH 7.0) which contains 6 mMole/liter calcium chloride.

Measurement of the prothrombin time.

The measurements are carried out at 37° C. and at a wavelength of 560 nm in a photometer with a cuvette holder which can be tempered and with an attached recorder. 1 ml. of reagent is pre-tempered to 37° C. and placed in a 1 cm. synthetic resin cuvette. 0.1 ml. of citrate plasma are pipetted in, immediately mixed and the recorder simultaneously started. The time is measured until an extinction increase of 0.1 extinction units has taken place.

A reference curve was determined according to this measurement process using pool plasma dilutions. The results obtained are given in the following Table:

| prothrombin time (in percent) of the samples | time in seconds up to an extinction change of 0.1 extinction units |
| --- | --- |
| 100% | 45.9 |
| 50% | 62.4 |
| 33% | 76.7 |
| 25% | 91.6 |
| 20% | 108.1 |
| 12.5% | 156.4 |
| 10% | 197.9 |

A comparison of the process according to the present invention and the process described by U. Becker et al. in Haemostasis, 12, 1–2, 73/1982 in which, instead of the compound of Example 2c), there was used Tos-Gly-Pro-Arg-p-nitroaniline acetate as indicator gave, for plasmas from anti-coagulated patients, an agreement with a correlation factor of 0.988.

EXAMPLE 18

Determination of the prothrombin time by means of remission photometric measurement Indicator mesh A nylon fabric Type NY75HC of the firm Züricher Beuteltuchfabrik, Zürich, Switzerland, is impregnated with a solution consisting of 2.5 g. Mowiol 26/88 (Hoechst AG, Germany), 150 mg. of the compound of Example 2c) and 110 mg. anhydrous calcium chloride ad 100 ml. water and subsequently dried at 50° C. in a drying cabinet.

Thromboplastin mesh

A nylon mesh Type NY75HC of the firm Züricher Beuteltuchfabrik, Zürich, Switzerland, is impregnated with a thromboplastin solution of the composition described below and subsequently dried at 50° C. in a drying cabinet.

The thromboplastin solution is prepared in the following way:

3.5 g. Mowiol 18/88 (Hoechst AG, Germany) are dissolved, together with 22 ml. of thromboplastin solution with which is achieved, in the case of a 100% plasma, a prothrombin time of 11.0–12.6 sec., in 100 ml. 100 mMole/l. hepes buffer (pH 7.45).

Indicator mesh and thromboplastin mesh are cut up into strips of 12 mm. breadth and, together with a 16 mm. wide glass fiber fleece, worked up according to European Patent Specification No. 0 208 218 and Federal Republic of Germany Patent Specification No. 36 10 429 to give a test carrier according to Federal Republic of Germany Patent Specification No. 36 16 496, as is illustrated in FIG. 1 of the accompanying drawings.

The test carrier illustrated in FIG. 1 has, in principle, the form of a conventional test strip. On a 100 mm. wide polystyrene film (1) is laid a glass fiber fleece (4) according to European Patent Specification No. 0 208 218 or Federal Republic of Germany Patent Specification 36 10 429 in a breadth of 16 mm. and partly covered with a coarse nylon mesh (3) and fixed on one end with an adhesive (2). On the free end of the glass fiber fleece are laid on top of one another the thromboplastin mesh (5) and the indicator mesh (6) and covered with a 200 μm. thick transparent polycarbonate film (7) of 16 mm. breadth and firmly stuck with an adhesive (8). The so produced bands are cut up to 6 mm. wide strips.

For measurement of the prothrombin time blood or plasma is applied to the covering mesh 3 and transported over the glass fiber layer 4 into the region of the thromboplastin mesh 5 and of the indicator mesh 6. In the case of the application of whole blood, there hereby takes place a separation of the plasma, as is described in European Patent Specification No. 0 045 476. In order to initiate the reaction with the reagents contained in the layers 5 and 6, these are pressed downwardly so that the sample liquid penetrates into these layers and the corresponding reactions takes place.

Further details regarding the chemical reactions which take place in the case of a coagulation test of the present kind are given in European Patent Specification No. 0 182 373.

With reagent carriers according to FIG. 1, on a remission photometer Reflotron ® (Boehringer Mannheim GmbH, Germany) with the LED for 567 nm, there is prepared a calibration curve with plasma dilutions. For this purpose, the plasmas are diluted with physiological saline to which has been added 10% bovine serum albumin, to give different prothrombin time percentages. The so pre-treated samples are diluted with physiological saline in a ratio of 1 part of sample to 6 parts of saline solution and 32 μl. amounts are pipetted ont to the application side (covering mesh 3 in FIG. 1).

The results for the determination of a reference curve are given in the following Table:

| prothrombin time (in percent) of the sample before the final dilution | time in seconds up to a remission change of 10% remission |
|---|---|
| 100% | 38.0 sec. |
| 50% | 57.0 sec. |
| 33% | 74.5 sec. |
| 25% | 93.9 sec. |
| 20% | 110.0 sec. |
| 12.5% | 163.8 sec. |

It will be understood that the specification and examples are illustrative but not limitative of the present invention and that other embodiments within the spirit and scope of the invention will suggest themselves to those skilled in the art.

We claim:

1. Method for determining a peptide bond cleaving enzyme comprising contacting a sample with a compound of the formula:

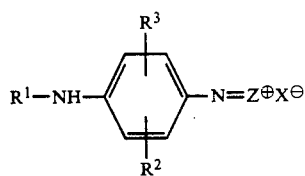

wherein $R^1$ is an amino acid residue or a residue of an oligopeptide in which amino groups are optionally substituted by protective groups, $R^2$ and $R^3$, which are the same or different, are hydrogen atoms, lower alkyl, lower alkoxy, carboxyl or lower alkoxycarbonyl or carboxamido groups having from 1-6 carbon atoms optionally substituted by lower alkyl or, if $R_2$ and $R_3$ are adjacent, can represent a —CH=CH—CH=CH— radical, and wherein Z is a radical of the general formula:

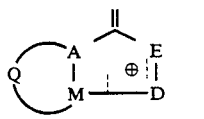

in which A, M, D and E are carbon or nitrogen atoms, whereby, insofar as they are not bridgehead atoms, said carbon atoms can optionally be substituted by oxygen, lower alkyl, lower alkoxy, aryl, aralkyl, or aryloxy, and said nitrogen atoms optionally substituted by lower alkyl, aralkyl or aryl, and Q is an unsaturated hydrocarbon chain with 3-5 carbon atoms which is optionally interrupted by nitrogen or sulphur atoms or contains such heteroatoms at the beginning or end of the chain, said carbon atoms optionally being substituted by lower alkyl, lower alkoxy, aralkyl, aryloxy or aryl and/or said nitrogen atoms optionally substituted by lower alkyl, aralkyl or aryl, and the total number of heteroatoms in the bicyclic radical is at most 3, and X is an anion of an organic or inorganic acid, and detecting one or more reactions products.

2. The method of claim 1, wherein said Z radical in said compound is selected from the group consisting of:

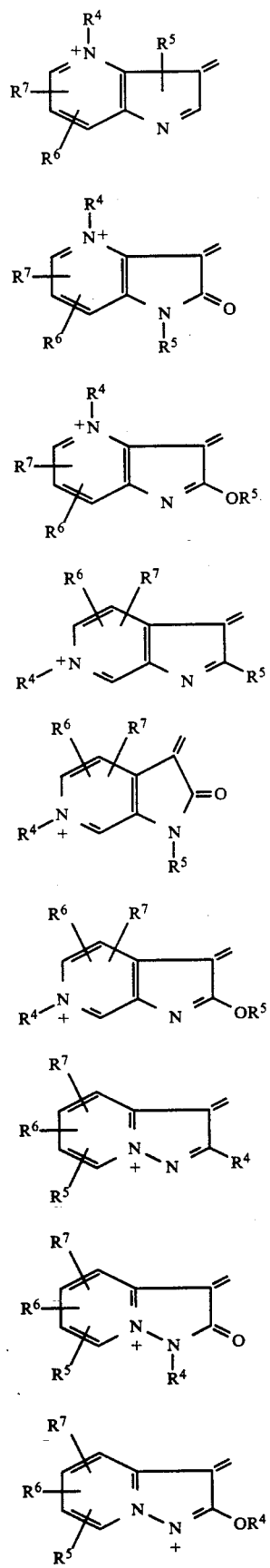

-continued

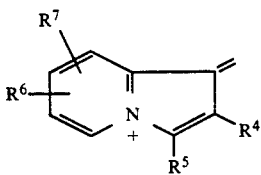

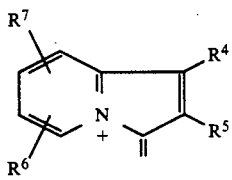

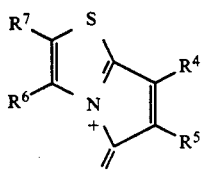

and

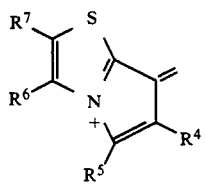

wherein $R^4$-$R^7$, which can be the same or different, are hydrogen atoms, lower alkyl or lower alkoxy of from 1 to 6 carbon atoms, aralkyl, aryloxy or aryl radicals.

3. The method of claim 1, wherein said amino groups of said compound are substituted by protective groups.

4. The method of claim 1, wherein said $R^2$ and $R^3$ groups of said compound are adjacent to each other and form the radical —CH=CH—CH=CH—.

5. The method of claim 1, wherein at least one of D and E in said compound is not a bridgehead atom, and is a carbon atom substituted by hydrogen, oxygen, lower alkyl, lower alkoxy of 1 to 6 carbon atoms, aryl, aralkyl or aryloxy.

6. The method of claim 1, wherein at least one of D and E in said compound is not a bridgehead atom, and is a nitrogen atom substituted by hydrogen, lower alkyl of from 1 to 6 carbon atoms, aralkyl or aryl.

7. The method of claim 1, wherein Q in said compound is substituted by nitrogen or sulphur atoms.

8. The method of claim 7, wherein said nitrogen or sulphur atoms are positioned at a point joining said A or M to the rest of said radical Q.

9. The method of claim 7, wherein at least one of said carbon atoms in said radical Q is substituted by hydrogen, oxygen, lower alkyl or lower alkoxy of 1 to 6 carbon atoms, aralkyl, aryloxy, aryl, or is bound to nitrogen within Q.

10. The method of claim 7, wherein at least one of said carbon atoms in said radical Q is bound within y to nitrogen and said nitrogen is substituted by hydrogen, lower alkyl of from 1 to 6 carbon atoms, aralkyl or aryl.

11. The method of claim 9, wherein two of said carbon atoms are substituted by lower alkyl radicals which form a saturated alkylene radical containing 3 to 5 carbon atoms.

12. The method of claim 1, wherein said compound is designated as 2H-1,4-dihydro-4-methyl-2-oxo-3-(4-tosylglycyl-L-prolyl-L-arginylamido)-phenylimino)-pyrrolo[3,2-b]pyridinium sulphate.

13. The method of claim 1, wherein said compound is represented by the formula:

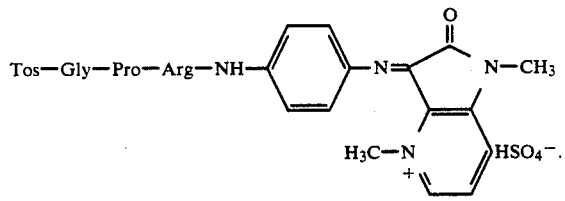

14. The method of claim 1, wherein said compound is represented by the formula:

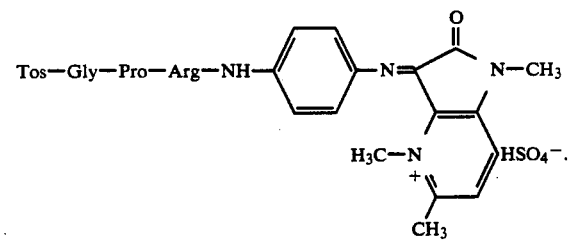

15. The method of claim 1, wherein said compound is represented by the formula:

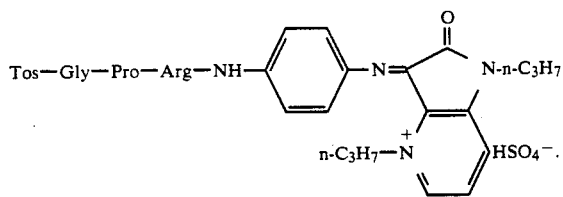

16. The method of claim 1, wherein said compound is represented by the formula:

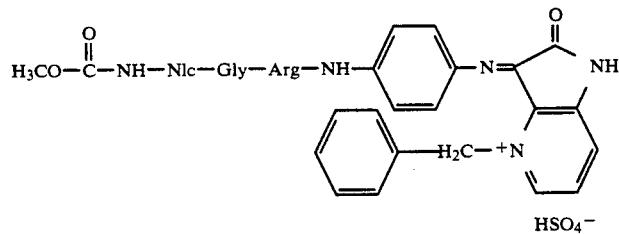

17. The method of claim 1, wherein said compound is represented by the formula:

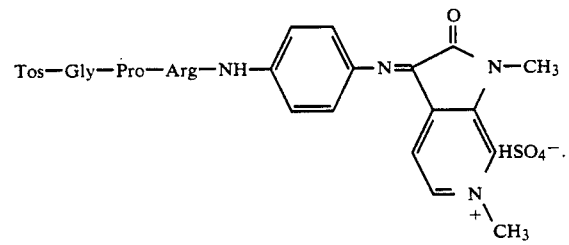

18. The method of claim 1, wherein said compound is represented by the formula:

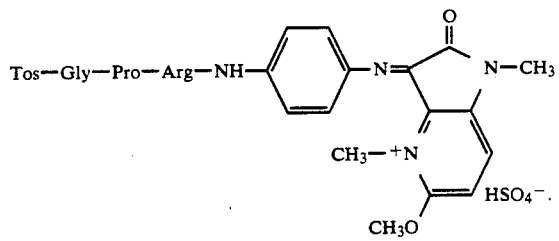

19. The method of claim 1, wherein said compound is represented by the formula:

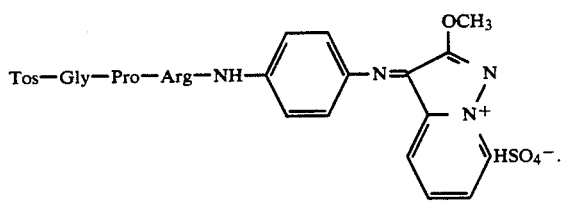

20. The method of claim 1, wherein said compound is represented by the formula:

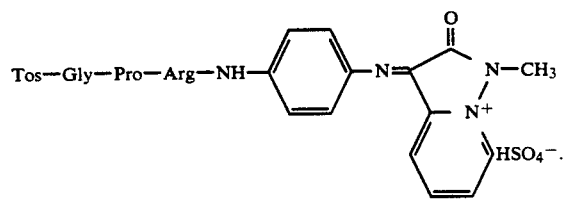

21. Method for determining the amount or the activity of a peptide bond cleaving enzyme, wherein said enzyme is a coagulation parameter, comprising contacting a sample with a compound of the formula:

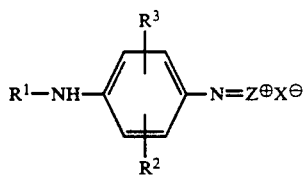

wherein $R^1$ is an amino acid residue or a residue of an oligopeptide in which amino groups are optionally substituted by protective groups, $R^2$ and $R^3$, which are the same or different, are hydrogen atoms, lower alkyl, lower alkoxy, carboxyl or lower alkoxycarbonyl or carboxamido groups having from 1-6 carbon atoms optionally substituted by lower alkyl or, if $R_2$ and $R_3$ are adjacient, can represent a —CH=CH—CH=CH— radical, and wherein Z is a radical of the general formula:

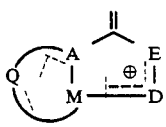

in which A, M, D and E are carbon or nitrogen atoms, whereby, insofar as they are not bridgehead atoms, said carbon atoms can optionally be substituted by oxygen, lower alkyl, lower alkoxy, aryl, aralkyl, or aryloxy, and said nitrogen atoms optionally substituted by lower alkyl, aralkyl or aryl, and Q is an unsaturated hydrocarbon chain with 3-5 carbon atoms which is optionally interrupted by nitrogen or sulphur atoms or contains such heteroatoms at the beginning or end of the chain, said carbon atoms optionally being substituted by lower alkyl, lower alkoxy, aralkyl, aryloxy or aryl and/or said nitrogen atoms optionally substituted by lower alkyl, aralkyl or aryl, and the total number of heteroatoms in the bicyclic radical is at most 3, and X is an anion of an organic or inorganic acid, and detecting one or more reaction products.

22. The method of claim 21, wherein said Z radical in said compound is selected from the group consisting of:

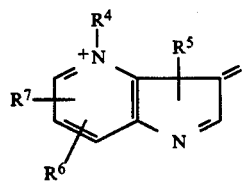

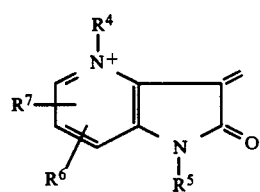

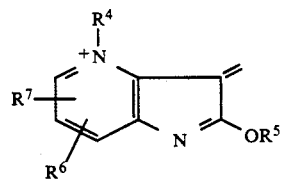

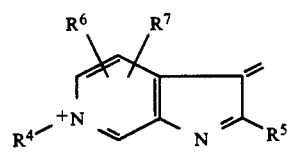

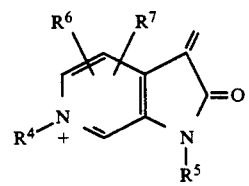

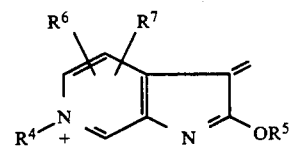

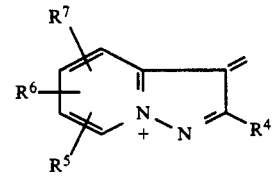

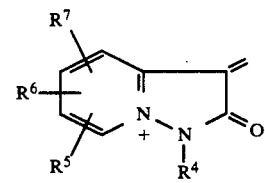

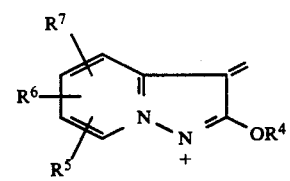

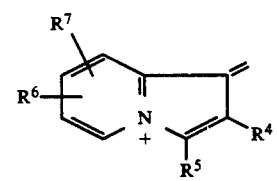

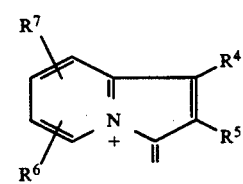

-continued

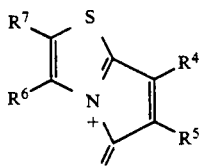

and

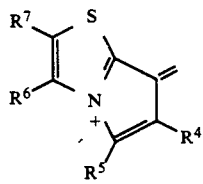

wherein R⁴-R⁷, which can be the same or different, are hydrogen atoms, lower alkyl or lower alkoxy of from 1 to 6 carbon atoms, aralkyl, aryloxy or aryl radicals.

23. The method of claim 21, wherein said amino groups of said compound are substituted by protective groups.

24. The method of claim 21, wherein said R² and R³ groups of said compound are adjacent to each other and form the radical —CH=CH—CH=CH—.

25. The method of claim 21, wherein at least one of D and E in said compound is not a bridgehead atom, and is a carbon atom substituted by hydrogen, oxygen, lower alkyl, lower alkoxy of 1 to 6 carbon atoms, aryl, aralkyl or aryloxy.

26. The method of claim 21, wherein at least one of D and E in said compound is not a bridgehead atom, and is a nitrogen atom substituted by hydrogen, lower alkyl of from 1 to 6 carbon atoms, aralkyl or aryl.

27. The method of claim 21, wherein Q in said compound is substituted by nitrogen or sulphur atoms.

28. The method of claim 27, wherein said nitrogen or sulphur atoms are positioned at a point joining said A or M to the rest of said radical Q.

29. The method of claim 27, wherein at least one of said carbon atoms in said radical Q is substituted by hydrogen, oxygen, lower alkyl or lower alkoxy of 1 to 6 carbon atoms, aralkyl, aryloxy, aryl, or is bound to nitrogen within Q.

30. The method of claim 27, wherein at least one of said carbon atoms in said radical Q is bound within Q to nitrogen and said nitrogen is substituted by hydrogen, lower alkyl of from 1 to 6 carbon atoms, aralkyl or aryl.

31. The method of claim 29, wherein two of said carbon atoms are substituted by lower alkyl radicals which form a saturated alkylene radical containing 3 to 5 carbon atoms.

32. The method of claim 21, wherein said compound is designated as 2H-1,4-dihydro-4-methyl-2-oxo-3-(4-tosylglycyl-L-prolyl-L-arginylamido)-phenylimino)-pyrrolo[3,2-b]pyridinium sulphate.

33. The method of claim 21, wherein said compound is represented by the formula:

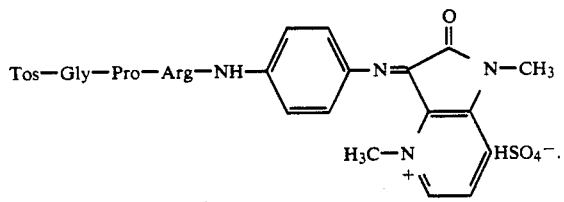

34. The method of claim 21, wherein said compound is represented by the formula:

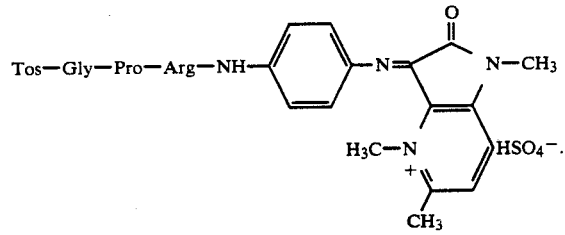

35. The method of claim 21, wherein said compound is represented by the formula:

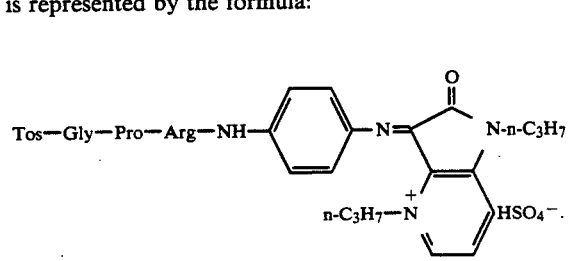

36. The method of claim 21, wherein said compound is represented by the formula:

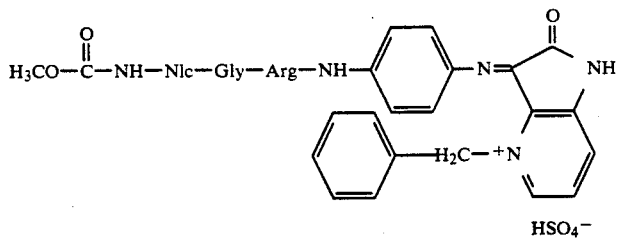
37. The method of claim 21, wherein said compound is represented by the formula:
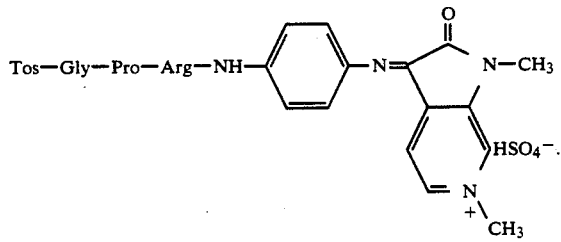
38. The method of claim 21, wherein said compound is represented by the formula:
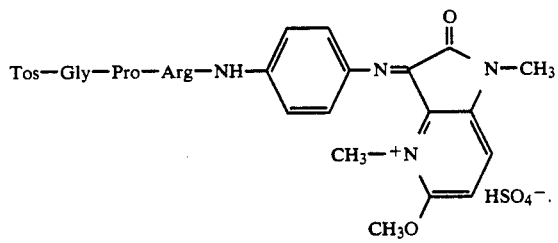
39. The method of claim 21, wherein said compound is represented by the formula:
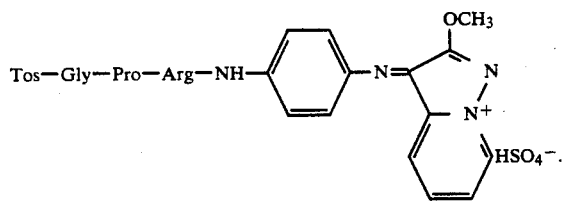
40. The method of claim 21, wherein said compound is represented by the formula:
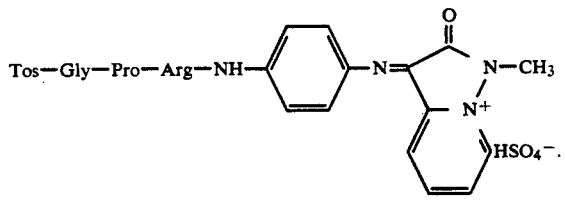
* * * * *

UNITED STATES PATENT AND TRADEMARK OFFICE
CERTIFICATE OF CORRECTION

PATENT NO. : 5,190,862
DATED : March 2, 1993
INVENTOR(S) : Wielinger et al

It is certified that error appears in the above-indentified patent and that said Letters Patent is hereby corrected as shown below:

Column 29, line 26, insert before "compound", --compound. As described in Example 4c), the nitroso--.

Signed and Sealed this

Nineteenth Day of July, 1994

*Attest:*

BRUCE LEHMAN

*Attesting Officer*     *Commissioner of Patents and Trademarks*